(12) United States Patent
Weinshilboum et al.

(10) Patent No.: US 6,265,561 B1
(45) Date of Patent: Jul. 24, 2001

(54) SULFOTRANSFERASE SEQUENCE VARIANTS

(75) Inventors: Richard M. Weinshilboum, Rochester, MN (US); Rebecca B. Raftogianis, Elkins Park, PA (US); Thomas C. Wood; Diane M. Otterness, both of Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 09/167,681

(22) Filed: Oct. 7, 1998

(51) Int. Cl.[7] ............................. C12N 15/54; C12N 9/10
(52) U.S. Cl. ...................... 536/23.2; 536/23.1; 435/193
(58) Field of Search ................................. 536/23.1, 23.2; 435/193

(56) References Cited

U.S. PATENT DOCUMENTS

| | | | |
|---|---|---|---|
| 5,733,729 | 3/1998 | Lipshutz et al. | 435/6 |
| 5,770,722 | 6/1998 | Lockhart et al. | 536/25.3 |

OTHER PUBLICATIONS

T.P. Dooley et al., "Genomic Organization adn DNA Sequences of Two Human Phenol Sulfotransferase Genes (STP1 and STP2) on the Short Arm of Chromosome 16", Biochem. Biophys. Res. Commun. 228: 134–140, Nov. 1996.*
Weinshilboum, "Phenol sulfotransferase in humans: properties, regulation, and function", Fed. Proc., 1986, 45(8):2223–2228.
Price et al., "Genetic Polymorphism for Human Platelet Thermostable Phenol Sulfotransferase (TS PST) Activity", Genetics, 1989, 122:905–914.
Weinshilboum et al., "Sulfotransferase molecular biology: cDNAs and genes", Fed. Proc., 1997, 11(1):3–14.
Hacia et al., "Detection of heterozygous mutations in BRCA1 using high density oligonucleotide arrays and two–colour fluorescence analysis", Nature Genetics, 1996, 14:441–447.
Campbell et al., "Human Liver Phenol Sulfotransferase: Assay Conditions, Biochemical Properties and Partial Purification of Isozymes of the Thermostable Form", Biochem. Pharmacol., 1987, 36(9):1435–1446.
Reiter et al., "Platelet phenol sulfotransferase activity: Correlation with sulfate conjugation of acetaminophen", Clin. Pharmacol. Ther., 1982, 32(5):612–621.
Wood et al., Human Liver Thermolabile Phenol Sulfotransferase: cDNA Cloning, Expression and Characterization, Biochem. Biophys. Res. Commun., 1994, 198(3):1119–1127.
Wilkinson, "Statistical Estimations in Enzyme Kinetics", Biochem. J., 1961, 80:324–332.
Cleland, "Computer Programmes for Processing Enzyme Kinetic Data", Nature, 1963, 198(4879):463–465.

Raftogianis et al., "Human phenol sulfotransferase pharmacogenetics: STP1 gene cloning and structural characterization", Pharmacogenetics, 1996, 6:473–487.
Ozawa et al., "Genetic polymorphisms in human liver phenol sulfotransferases involved in the bioactivation of N–hydroxy derivatives of carcinogenic arylamines and heterocyclic amines", Chem. Biol. Interact., 1998, 109:237–248.
Terwilliger and Ott, "Linkage Disequillibrium between Alleles at Marker Loci", Handbook of Human Genetic Linkage, The Johns Hopkins University Press, Baltimore, 1994, 188–193.
Lewis, "PCR's Competitors Are Alive and Well and Moving Rapidly Towards Commercialization", Genetic Engineering News, 1992, 12(9):1 (3 pages).
Guatelli et al., "Isothermal, in vitro amplification of nucleic acids by a multienzyme reaction modeled after retoviral replication", Proc. Natl. Acad. Sci. USA, 1990, 87(5):1874–1878.
Weiss, "Hot Prospect for New Gene Amplifier", Science, 1991, 254(5036):1292–1293.
Van Loon and Weinshilboum, "Thiopurine Methyltransferase Isozymes in Human Renal Tissue", Drug Metab. Dispos., 1990, 18(5):632–638.
Van Loon et al., "Human Kidney Thiopurine Methyltransferase Photoaffinity Labeling with S–Adenosyl–L–Methionine", Biochem. Pharmacol., 1992, 44(4):775–785.
Kohler et al., "Continuous cultures of fused cells secreting antibody of predefined specificity", Nature, 1975, 256(5512):495–497.
Kozbor et al., "The production of monoclonal antibodies from human lymphocytes", Immunology Today, 1983, 4(1):72–79.
Cote et al., "Generation of human monoclonal antibodies reactive with cellular antigens", Proc. Natl. Acad. Sci. USA, 1983, 80(7):2026–2030.
Huse et al., "Generation of a Large Combinatorial Library of the Immunoglobulin Repertoire in Phage Lambda", Science, 1989, 246:1275–1281.
Short Protocols in Molecular Biology, Chapter 8, Green Publishing Associates and John Wiley & Sons, Edited by Ausubel, F.M. et al., 1992, 8–1—8–25.
Short Protocols in Molecular Biology, Chapter 11, Green Publishing Associates and John Wiley & Sons, Edited by Ausubel, F.M. et al., 1992, 11–1—11–54.
Cole et al., "The EBV–Hybridoma Technique and its Application to Human Lung Cancer", Monoclonal Antibodies and Cancer Therapy, Alan R. Liss, Inc., New York, 1985, 77–96.

(List continued on next page.)

Primary Examiner—Rebecca E. Prouty
(74) Attorney, Agent, or Firm—Fish & Richardson P.C.

(57) ABSTRACT

Isolated sulfotransferase nucleic acid molecules that include a nucleotide sequence variant and nucleotides flanking the sequence variant are described. Methods for determining a risk estimate for hormone dependent disease and methods for determining sulfonator status also are described.

3 Claims, 13 Drawing Sheets

OTHER PUBLICATIONS

Raftogianis et al., "Human Phenol Sulfotranferase Pharmacogenetics: Association of Common SULT1A1 Polymorphisms with TS PST Phenotype", *ISSX Proceedings—8th North American ISSX Meeting, Hilton Head, South Carolina*, 1997, 12:96, Abstract.

Raftogianis, "Human Phenol Sulfotransferase (PST) Pharmacogenetics: Analysis of SULTA1 and SULT1A2", *Clin. Pharmacol. Ther.*, 1998, 63(2):224.

Her et al., "Human Sulfotransferase SULT1C1: cDNA Cloning, Tissue–Specific Expression, and Chromosomal Localization", *Genomics*, 1997, 41:467–470.

Raftogianis et al., "Phenol Sulfotransferase Pharmacogenetics in Humans: Association of Common SULT1A1 Alleles with TS PST Phenotype", *Biochem. Biophys. Res. Commun.*, 1997, 239:298–304.

Raftogianis et al., "Phenol Sulfotransferase (PST) Molecular Pharmacogenetics", *Clin. Pharmacol. Ther.*, 1997, 61(2):234.

Raftogianis et al., Human Phenol Sulfotransferases SULT1A2 and SULT1A1, *Biochem. Pharm.*, 1999, 58:605–616.

* cited by examiner

```
        ttgctgcag ctgcctctcc otcottgtot cttacotgco tgctgoctgg gacaggatga agcggggcoc ttgtgttgcc ccaacoctgg ctgttgcta
   101  tgatctgcct gtgagaggag ttccttccgg aagaaccagg gcagcttctg ccctagagg gcaatgccc tagctgagtg cagtocccg
   201  agagcccaag ggtccagtt tgggaagagg gtgcccagtt gtgcaatcca ggcggggca gcgtgtcct gatctggta ttcagggctg agcctggagg
   301  gcccagcct ggtcctgactc totctocctc totggcccca tgcottggtt gctgtgaggc gtcactgctt tggtgacct gatctggctg tgatgatga
   401  gggcttgtga tgcctgactc totctocctc totggcccca gagtggctt gagtggcctt tgcctacc cctggctgc ctgtgaccaa aaacggtgg
   501  gcacggggga aatagtggaa gactggaat tagaagacgt cagtgtccct aatccctcc agatactgt ggcctaggg agtcatcaa aatggggtga
   601  cctcgtttct gcaggcacac tggatagcc tgctggagct cagtgccag aatcccctcc agatactgt gcctgcacc aggttgcaa
   701  gacatcgacc tcagccgtt tcacgcttt ttttgttt ttttttttt ttgagacga gattccagg gattccagg gtgtgcacc aggttgact
   801  tottgctca ccgcaacctc cgcctctgg gttcaagcga ttctcctgcc tcacttgcc tcagctggct tggggctcct tcgatactc cgtgatcc
   901  aattttotat tttagtgca gacaggttt ctccatgtt ggcttctc agctcttgg tctcaaacto cacctagcc agaaacatt taaggacaag tgaatgtag
  1001  gggagttcc tgagagtaa cacgtgcca aggactcac ggctccc tcaagacct agaacaat caccgtgcca gtcgtcaga ggtgtggc aatacggtg
  1101  ggctttoct aactaaagag gggtatatttc atgaagtc cagaaaaag caagatttc atcataacat gagaaacta caccaaatac agcgcatgt
  1201  ttoctggag ogtcttggca otgtggtg tacgttca tatgttactg attattggc cttagcgat gcagctattt caagttcct tcttcctc
  1301  tgtgtctggt tggtcgtggc cagcttgtc ctcatoctat ttttcaggga atctccacatt ctcgctgtcat cctgtgg gtccgacag
  1401  atgtgaaact gctgcctgg atttgtatt cactgctac ctctgaggg ctctgagg catatagcc gctagtagcc tgaggactg ccagtcagg
  1501  ttgttactag agtgcaatac aaagtcttag tcaaggaac ctctgaggc gcctagcat atgagaagcc tctctcctgc cctgtcctcc cttcctctcc
  1601  ggattcctca tgggcacaga ggagggaga gggtgcact agcgattct tggaagtot gggagattca ccttactca gatggtgtt tacctgtctc gtgaacagct
  1701  actcccacct gtcccgttgc ctctgaacto aggacctc aggggatg ccccctttca aggggcctg tggttccaa actcggcct ctgtggtot
  1801  tgacccttga ctttaaagtg aggataaaga acgagagg tgggggatg cacctgccac gggttgtgt tottotatca atgttctg aggtccccag
  1901  ctgtctgtg gacgctctt caaaccaag gaaataaaac caaccccagg caactgccct tgttctttct atccatgctc tgtccaccc ctgccctcc
  2001  gagccatgaa gctgggctg actccatcc tctagactgg ccttggtgtc agagcctgga gtcatgggc tgtgggggc ctgggctg cactggcca gaaccctgg
  2101  actctgccca cacacatccc tctagactgg cottgtgtc tgtcaggc agtctccc agctttctcc ccctctctt ccctctctt gctggtca
  2201  caccttcaag actggcctgc agccagcagg tagtgacct ttccaggcc aggtcaggg ccaagtcaga ccaatgaca ccagtgaa gtcggaaaa aaaaaaaa
  2301  attagagaga ggttgtctgt tgctgccctg gggtggtga gttcaggggc tttccccttt cattctctg ttttctacac agaaaactca gtgtggctt tggagatcac
  2401  cagaaaaaaa aacctacaaa aacaaccca ccattgggc ccatgggc tttccccttt cattctctg acccaccco ttccttccgg agcaaactca agcaatct aagtcagcc
  2501  tttaagcttg totccagctg gcacactaag gagggtaatg gaggtaatg gagaagctcc
```

```
-3729  ctctcctcc ttgtctctta cctgctgct gctgggaca ggatgaagcg gggccttgt gttgcccaa ccctgctgt tggctaagag cccagtgat
-3629  ctgcctgtga gaggagttcc ttccggaaga acaggtgca cttctgccc tagagggca atgcctagc tgagtgcagt ccccgcccc cagcctggtc
-3529  cagctttggg aagagggtgc ccagttgtgc aatccaggcc gggcagccg ttggtattca ggctgagcc ggctgagcc tggaggggc ttgtgatgcc
-3429  tgactctgtc tctctctctg gcccatgcc ttggtagctg tgaggcgtca ctgtttggg tgacctgatc tgctgtgat ggatgagac ggggaaata
-3329  gtggagact cggaattaga agactgagt gggctttggc tgcccact actgtggcc cctgtcctg ggctgcctgt gaccaactt gtttctgcag
-3229  gcacactgga tagccctgct ggagcctgct gtccctaatc cctccagat actgtggcc tagggaggt catcaaagac cagtgggaca tcgacctcag
-3129  cctgttcca cgttctttgt tgtttttttt ttttgtgga gacagagttt cactcttgtt gccaggctg gagtgcaatg ggtgatctt ggctcaccgc
-3029  aacctctgcc tcccggttc aagcgattct cctgcctcag cctcccagt agctggatt acaggcgtgt gccacaggc ttgactaatt ttctattttt
-2929  agtagagaca aggtttctcc atgttggtca ggctgtctc aaactccga cttcaagtga tctgcctgcc tcggcctccc aaagtgctgg gattacagga
-2829  gtgagccacc gtgcagcc ttctccagc tcttggcacc ttagccagaa acaatttaag gacaagtgca aaagtcatga acgtaggcag attcctgca
-2729  gagtaaaggg actcactgaa gaagaagaac gtgggggtcc tcaagagagt gtctcatgcc ctacaagtg ctacaagtg ctttatggc ttcttcaact
-2629  aaagaggggt atattcatga agagtccagg aaaaggtaaa gatttctcaa gattctcata cacagccaat cacccaata cagtgttcc tgagcgtc
-2529  ttggcactgg tgggtgtacg gtttcatatg ttactgattg tacagtgaga tcctaggtga gaccgtggtg gacgtggtg ocatgttgct totgttgct
-2429  cgagccagc ttggcctca tcctatttt cagggactta ttggccttg gcacatgcag cctcttct ctgtggtcc ctgtcatgt gaactgctg cactagagtg
-2329  cctggatt tctgttgtct tgctagaact ctattatct cacattctg cctcttct ctgccacccc gggtgttttt tcatgggat tcctcagggg
-2229  caatacaaag tctcagtcaa gaggcctcc tgaagttgc tgaaggcagg ggtgagcta ctctgctgg gatgccgag cctcagttt ccccgcttgc ctctgagtc
-2129  cacagaggag ggaggaggg cctgtgccc tagcaggga cagcctctc gcagctctc ctctgctgg gccccagt saaatcccatg gtgccagt cttaaatag tgagacaaa
-2029  acgcaacct gggaaggtt gggagactca cttactca gatgttgtt tcctgtctc gtgccagt tgccctgta cccccttgc tgagcctcc ttcaaaccca
-1929  gaacgagag gggtgggga tgcactctt cccagggc ccacctctt cccacttgtc tgagcctcc tgagcctcc tgagctggg gaagctggg ctgcctcca
-1829  tggaagaaaa agtacctgcc agggcttgtg gttcttctag gatcttctat cgattgtctg tagctccc cttcactctg ccacacgca tcactccaga
-1729  gggcaatggg actgcagtgt ccttgttctt atggatccat gctctgtcc acccctgcc ttcactctg caagacctt caagactggc ctgaggccag
-1629  ctgccttgt ggtcagagc tggagtgcat gggctgctgg aggctgctgg gttgactgg gttgactgg gcaagaccc tcttgctgg gtcaattaga gaaagcttgt cttttgagt
-1529  caggtagttg accttttcag ggcctgcta tcccagcttt ctcaaaaaaa cctcccto tcttgctgg accattggc ccttccct ttcattctc tgttctctac
-1429  tcaggggcag gtcagagcc cagtgacagc tcaaaaaaaa aacccaaaa gttgactgg gcaagaccc tagaagct cccaccc caaccctacc
-1329  acaccaaacc cagtcgtggc tttggagatc actttaagct tgtctccagc aggagggtaa tagagaagct
```

```
   1 acctctgcct cctggttcca agcaatcctc cttcctcacc ctccagagta gctgggatta
  61 cacgcgcctg ccaccgcgcc tggcctaatt tttgtatttt tagtagagat ggggqtttcc
 121 aaccatgttg gccaggctgg tctccaaact cctgacctca ggtgatcctg cccacctaag
 181 cctcccaaaa tgctggtatt acaggcatga gccaccgtgc ccggcctaaa taattaataa
 241 aataatggac gatgggtgcc ttctactgag ctcccggtaa ttgtgagtga gtagaggact
 301 tgccctgggg acattcagtg acctgctggg tgttgctgag ctgtgaggaa gttcaggtct
 361 ggctgcagtg gtgaggctgt gactcaatca atcactgctg atgctcccag gacctgcacc
 421 agcttagtcc tagggcaag gattttaact gtccacctca gtttcttcat ttgtaagatg
 481 caaataacag tcaccctgc ctcatgggat ggagctgtgt aatgcccgca acagtgcctg
 541 ctgcatagag gggttgctgc cagctgcctc tccctccttg tctcttacct gcctgctgcc
 601 tgggtcagga tgaagaccag ccc ttgtgtt gccccaccc tggctgcctg ctaagggccc
 661 atgtgatctg cctggcagag gagtttcttc aggaagaacc agggcagctt ctgccctag
 721 agggccaatg cccttg gtga gtgcagtccc ctggccccag cctggtccac ctctgggaag
 781 agggtgccca gttgtgcaat ccaggcccag gcagctgagc cctcatctca gcatgcaggg
 841 cggatactgg aggggcttg tggcatctga ctctgtatct cctacctgcc cctctccttg
 901 gtag ctgtga aagtcactg ctttggggag acctgatctg gctgtgccag atggacactg
 961 agaaagaagt agaagactca gaattagaag a gtgagtgg gctttggtgg cgggctccct
1021 accccactcc ctgccctggg ctgcctgtga ccacactgct tgcctctgca ggcacactgg
1081 acagacctgc tggagacctg atcctcagtg tccttacccc ctcctacctc ttttctgtgc
1141 cacctgctgt gggtccagca ggttttact tgagtacaat aaaaagtctg agtcaagggt
1201 gccttatggt ggatgctgag ggaggggcg gagctagtag cccaaggtcc tgccagtcac
1261 ggggcttcct caggggcaca gaggaggcag gagggccccc tggccctagc acgtgaacag
1321 cttctactct gcctggaaac cccatgcctc agctttcccc tacttgcctc tgagctcatg
1381 caattcttgg aagcctggga gacttacctt gaaattgaat gcaaatagga caaagaccaa
1441 ggaggatggg gggatgccct ccttccacgg ggccctgtgg cttccaagtc ttaatctcct
1501 ctagtctctt gtctacggag cctccttcaa acccagggaa agaaaagcac ctgccagggt
1561 tgttttcttc ctaggatctt ctattgatgc tctgtgaggt cccccaggag ccatgaagct
1621 agggctggct cctagggcaa tgggactaca gtgtcctgt ccttcttat tcttttcgtt
1681 cttctttct ttctttttt ttttttttt ttttttgag acagagtctc actctgttgc
1741 ccaggctgga gtgcagtggt gtgatcttgg ctcactgaaa cctccgcctc ctgggttcaa
1801 gtgattctct tgcctcagcc tcctgagtag ctaggattac aggtgccgc catcatgccc
1861 agctaatttt tgtattttta gtagagacag ggtttcacca tgttggccag cttggtctcg
1921 aactcctgac ctcaggtgat cctgctgcat cgacctccca aagtactggg attacaggcg
1981 tgagccacca cgctcagcct cttcttgtt ctatatgtcc atgctctgct ccacttctgc
2041 cccttcactc tgccccacac atcactccag actggccttg tggtcagagc ctggaatgcc
2101 tgggctgctg ggggcctgtg gactgcactg gccagaacc ctgccgcct tcaagactgg
2161 cctgtagcca gcaggtaggt gacttttccc aggccggcct atcccacctt tccctccac
2221 tcactcacct cccttgcctg ggtcaattag agaaagcttg tcggccaggc atggtggctc
2281 atgcctgtaa tctcagcact ttgggaggcc gaggcgggcg gatcatctga gctcaggagt
2341 ttgagaccag cctggccaac atggcaaaac cccgtctcta ctaaaaatac aaaaattaac
2401 cggatgtggt ggtgtgcacc tgtaatccca gctactcggg aggctgaggc agaagaatcg
2461 cttgaaccca ggaggggag gttacagtga gcggagatcg tgctactgca ttgcagcctg
2521 ggcgagagag cgagtctcca tctcacataa aaaaagaaa agaaagaaa gcaagcttgt
2581 ctgttggcct gccctgcagg gtggagttca gagggaaggt caggagccta gtgacagctc
2641 aaaaaaaaaa aacccaaat accaatgttg gccccttttg ccttcattc atgtgttttc
2701 tatacactaa actcacatat tgggtttgca gatcactcca agcttggctg gagctgtggt
2761 ggtaaggagg gtaatagaga agcttcccca ccctcaaccc cacccttcc ttcctggagt
2821 tcccagccct gactttagat ccctcc aca ctggaccttc aaaacccctca gggcagagag
2881 cagccctaca ctccctacac cacaccata ctcagcccct gcaggcaagg agagaacagg
2941 tcaggttccc gagagctcag gtgagtgaca cgttggaatg gccagggca ccttcacccct
3001 gctcagcttg tggctccaac attctagaag ccgaggcctc tgccatccct gcctttccc
3061 atggatattc catttcaatt agacaaccca gcctggccgg aaccccctg cgttccttct
3121 ttccctttgt gtatttttga gacagggtgt tgctccgtca cccaggctgg agtgtagtgg
3181 gatcctggcc cactgcagcc tcaaattcct aggctgaggc aatcctgccg cctcagcctc
```

FIG. 7A

```
3241 ctgagtagct ggggttacaa gagcaagcca ccacacccag ctaattttga aaaatatttt
3301 ttgtagagga gaggtcttgc tttgttgtcc aggttggtct caaactccag ggctcaaggg
3361 atcctttccc gttggcctcc caaggctctg ggattacagg cgggagtcac cctgcctggg
3421 cccctccttt tgatgagtca tcagttttca ttccgcacg aggctctagc cctggtacc
3481 agcttagttg ctcaatgggc tgtgtttgtt ctggagccca gatggactgt ggccaggcaa
3541 gtggatcaca gacctggccg gcctgggagg tttccacatg tgagggcat gagggggct
3601 caaggagggg agcatcgggg agaggagcgc actgggtgga ggctggggt cccagcagga
3661 aatggtgaga caaagggcgc tggctggcag ggagacagca caggcaggcc ctagagcttc
3721 ctcagcacag ctggactctc ctggagacct tcacacaccc tgatatctgg gccccgcgct
3781 acgagggtgc tttcactggt ctgcactatg cccaggccc tgggattttg aacagctctg
3841 caggtgactg aaaggtgcgg ccaggctggg aacgacctg gtttcagccc cagccccgcc
3901 actgactgac tttgtgagtg cggcaagtc actcagcctc ctaggcctc agtgacttcc
3961 ctgaaagcaa aaactctgca aaggggcagc tgggtgctgg ctcacacctg taatcccagc
4021 actttgggag gctgaggtag acaaatcact tgaggccagg agtctagac cagcctggcc
4081 aacatggtga aaccccatct ctactaaaga aaaaaaaaa ttagctgagc atggttgtac
4141 atgcttgtaa tcccagctac ttgggatgcc gaggcgggag gattgcttga acccaagagg
4201 tggagtttgc agtgagctga gattgtgcca cactgcactc cagcttgggt gagagtgaga
4261 ctccatctca aaaaaaaaaa aaaagagaa gaatcccact ttcttgctgt tgtgatggtg
4321 gtaagggaac gggcctggct ctggcccctg atgcagaac atggagctga tccaggacac
4381 ctcccgcccg ccactggagt acgtgaaggg ggtcccgctc atcaagtact ttgcagaggc
4441 actggggccc ctgcagagct tccaagcccg acctgatgac ctgctcatca acacctaccc
4501 caagtctggt aagtgaggag ggccacccac cctctcccag gcggcagtcc ccaccttggt
4561 cagcaaggtc gtgccctcag cctgctcacc tcctatctcc ctccctctcc acgcaccacc
4621 tgggtgagcc agatactgga catgatctac cagggcggcg acctagagaa gtgtaaccgg
4681 gctcccatct acgtacgggt gcccttcctt gaggtcaatg atccagggga accctcaggt
4741 gcatggctgg gtcctggggg taagggaagt ggaggaagac agggctgggg cttcagctca
4801 ccagaccttc cctgacccac tactcaggc tggagactct gaaagacaca ccgcccccac
4861 ggctcatcaa gtcacacctg ccctggctc tgctccctca gactctgttg gatcagaagg
4921 tcaacgtgag gccggctca atggttcaca cctgtcatcc cagtttgaga ctgaggaggg
4981 aggatccctt gaaggcgaga gatggagacc agcctgggca acattgctgt agagatgaca
5041 tccatctct acaaaaataa aattaacaac ctggtatggt ggcatagact gttcccagtt
5101 acttaggagg ctcagcgggg aggactgttt atgcaaatag gaagctgcaa tgagccctga
5161 tgatcctgct gctgcactcc agcctgggca acacagcaaa accatctcta cgaaaaaaaa
5221 agttcccact gactggcaag gaaagccagg aaggggggct caggtgccct ctcagccatg
5281 tacctgttct tctggaaggg cctcctcgct tctgccaggc tcatcacatc tttttttttt
5341 ttgagacaga gtcttgctct gtcaccctgg ctggagtgca gtggcatgat ctcagctcac
5401 tgcaacctcc gcctcccag ttcaagtgat tctcctgcct cagcctcctg agtagctggg
5461 attacaggcg tgtgctacca cacccggcta atttttgtat tcttttagt agagacgggg
5521 tttcaccatg ttggtcaagt ggatctcaaa ctcttgacct tgtgatcctc ctgcctcgac
5581 ctcacaaagt gctggaatta caggcgtgag ccaccgcgcc tggccctttt ttttttgag
5641 acagtttcac tcttgttgcc gaggctagag cgcaatcgtg tgatctcggt tcactgcaac
5701 caccgcctcc tgggttcaag caattctcct gcttcagcct cccaaggagc tgggattaca
5761 ggtacctgcc accacgcccg gctaattttg tatttttagt agagatgggg tttcaccatg
5821 ttggtcaggc tggtcttgaa ctcctgacct caggtgatct ggccttgg cctcccaaag
5881 tgccgggatt agaggcatga gccaccacgc ccagccttca tcacatcttg agagaggaca
5941 ctgtctgcct cttgctctga tgagggtctg atgcaaagga tagtgagtct ctacagtgca
6001 cacttaagaa aggcagcatg tgggtgctca caggtcaggc ggaggagggg gagctggtgg
6061 ggaccaggca tgccttgctc cagatcagga tatgatggca ttggtgcaga ttatattagt
6121 atagaatatg gtctcaggaa ccaggcagga ctttggcttc cgagcagggt tcagatccca
6181 gcttggccct acctgtgcag tgagatctca agcaagtcag cctctaagcc tcaggttcct
6241 cccttgccag ttcaacagat gagctggcct ggggtgggct gtgtggtgat ggtgctgggg
6301 ctgggtcctc tgccctgca ggtggtctat gttgcccgaa acccaaagga cgtggcggtc
6361 tcctactacc atttccaccg tatggaaaag gcgcaccctg agcctgggac ctgggacagc
6421 ttcctggaaa agtcatggc tggagaagt gggcttgact ggaggaagga gggtgtgaag
6481 ccgaggggtg gtggctataa cgtacagcaa ccctgtgtcg gtgcccctg cccgcttctc
6541 tactgtccta cgggtcctgg taccagcacg tgcaggagtg gtgggagctg agccgcaccc
6601 acctgttct ctacctcttc tatgaagaca tgaaggaggt gagaccgact gtgatgcttc
```

FIG. 7B 6661 ccccatgtg acacctgggg gcaggcacct cacagggacc caccaaggcc acccagcccc
6721 gtccctgggc ggctcccaca gcaagcccgg attccccatc ctacctccct ggcccaggcc
6781 ccccactgc agccccacct ggcagcaggc tcggcacagc tttcatcttc tgcacctgag
6841 tcagctgcat gggtggccac ggatcagata cttagtccta ttgcttatcc tcaccaaagj
6901 gtgtgccacc cagggccaca gtcatggaag aagaccatcc cggtcctcac ccataggcgc
6961 caagccctgt tcatgatggg atcacagggc agagatcaat tcattttact cca_agacta
7021 gggcccagg ggttgaggct ctttggggtt tctaggggaa gtggccagat cccctctgag
7081 gttagagagg gggacccgtt ttgtttgct ccactgagga gccctctgct gctcagaacc
7141 ccaaaaggga gattcaaaag atcctggagt ttgtggggcg ctccctgcca gaggagacca
7201 tggacttcat ggttcagcac acgtcgttca aggagatgaa gaagaaccct atgaccaact
7261 acaccaccgt cccccaggag ctcatggacc acagcatctc cccttcatg aggaaacgtg
7321 ggtgctggcc agcacggggg tttggggcgg gtgggagcag cagctgcagc ctccccatag
7381 gcacttgggg cctcccctgg gatgagactc cagctttgct ccctgccttc ctccccacg
7441 catggctggg gactggaaga ccaccttcac cgtggcgcag aatgagcgct tcgatgcgga
7501 ctatgcggag aagatggcag gctgcagcct cagcttccgc tctgagctgt gagaggggct
7561 cctggagtca ctgcagaggg agtgtgcgaa tctaccctga ccaatgggct caagaataaa
7621 gtatgatttt tgagtcaggc acagtggctc atgtctgcaa tccagcgat ttgggaggtt
7681 gagctggtag gatcacaata ggccacgaat ttgagaccag cctggtaaaa tagtgagacc
7741 tcatctctac aaagatgtaa aaaaattagc cacatgtgct ggcacttacc tgtagtccca
7801 gctacttggg aagcagaggc tggaggatca tttcagccca ggaggttgtg gatacagtga
7861 gttatgacat gcccattcac tacagcctgg atgacaagca agaccctccc tccaaagaaa
7921 ataaagctca attaaaataa aatatgattt gtgttcatgt agagcctgta ttggaaagga
7981 agagaaactc tgagctgaaa gagtgaatgc ccggtggggc cacatatggt cacctctccc
8041 ccagccttca gctccccagg tcaccatatc tggggagggg agaagggttt ggagaagtaa
8101 aacccaggag atgtgtggag gggggatgtc tgtttaatcc cagcacatcc tctgctgtcc
8161 tgcccaaga tggtggagga cgtcgagtcc gccggcagc gtcacttttt cttgggctcc
8221 ttagaagcta ccaggtacct ctgggccaca ctgagatgag gggagtagcc gcctgcatag
8281 gaggtgtctt caaacaggat agtatagtcc ctcctggggg ttgtgggggt aggtggccaa
8341 ggaagggtag aggagcaagc ccccgggct ggttgtcaac tcactttgtt ggctggaatt
8401 ggttgtaact tgaccacctc gggcaggatc ccactgctca tcccaa

FIG. 7C

SULFOTRANSFERASE SEQUENCE VARIANTS

TECHNICAL FIELD

The invention relates to sulfotransferase nucleic acid sequence variants.

STATEMENT AS TO FEDERALLY SPONSORED RESEARCH

Funding for the work described herein was provided by the federal government, which has certain rights in the invention.

BACKGROUND OF THE INVENTION

Pharmacogenetics is the study of the role of inheritance in variation of drug response, a variation that often results from individual differences in drug metabolism. Sulfation is an important pathway in the metabolism of many neurotransmitters, hormones, drugs and other xenobiotics. Sulfate conjugation is catalyzed by members of a gene superfamily of cytosolic sulfotransferase enzymes. It was recently agreed that "SULT" will be used as an abbreviation for these enzymes. These enzymes also are known as "PSTs" in the literature. Included among the nine cytosolic SULTs presently known to be expressed in human tissues are three phenol SULTs, SULT1A1, 1A2 and 1A3, which catalyze the sulfate conjugation of many phenolic drugs and other xenobiotics.

Biochemical studies of human phenol SULTs led to the identification of two isoforms that were defined on the basis of substrate specificities, inhibitor sensitivities and thermal stabilities. A thermostable (TS), or phenol-preferring form, and a thermolabile (TL), or monoamine-preferring form, were identified. "TS PST" preferentially catalyzed the sulfation at micromolar concentrations of small planar phenols such as 4-nitrophenol and was sensitive to inhibition by 2,6-dichloro-4-nitrophenol (DCNP). "TL PST" preferentially catalyzed the sulfation of micromolar concentration of phenolic monoamines such as dopamine and was relatively insensitive to DCNP inhibition. Weinshilboum, R. M. *Fed. Proc.*, 45:2223 (1986). Both of these biochemically-defined activities were expressed in a variety of human tissues including liver, brain, jejunum and blood platelets. Human platelet TS PST displayed wide individual variations, not only in level of activity, but also in thermal stability. Segregation analysis of data from family studies of human platelet TS PST showed that levels of this activity as well as individual variations in its thermal stability were controlled by genetic variation. Price, P. A. et al., *Genetics*, 122:905–914 (1989).

Molecular genetic experiments indicated that there are three "PST genes" in the human genome, two of which, SULT1A1 (STP1) and SULT1A2 (STP2), encode proteins with TS PST-like activity, SULT1A1 (TS PST1) and SULT1A2 (TS PST2), respectively. The remaining gene, SULT1A3 (STM), encodes a protein with TL PST-like activity, SULT1A3 (TL PST). DNA sequences and structures of the genes for these enzymes are highly homologous, and all three map to a phenol SULT gene complex on the short arm of human chromosome 16. Weinshilboum, R. et al., *FASEB J.*, 11(1):3–14 (1997).

SUMMARY OF THE INVENTION

The invention is based on the discovery of several common SULT1A1 and SULT1A2 alleles encoding enzymes that differ functionally and are associated with individual differences in phenol SULT properties in platelets and liver. In addition, the invention is based on the discovery of SULT1A3 sequence variants. These discoveries permit use of SULT genomic and biochemical pharmacogenetic data to better understand the possible contribution of inheritance to individual differences in the sulfate conjugation of drugs and other xenobiotics in humans. Thus, the identification of SULT allozymes and alleles allows sulfonator status of a subject to be assessed. The information and insight obtained thereby allows tailoring of particular treatment regimens in the subject. In addition, risk estimates for hormone dependent diseases can be determined.

The invention features an isolated nucleic acid molecule including a SULT1A3 nucleic acid sequence. The sulfotransferase nucleic acid sequence includes a nucleotide sequence variant and nucleotides flanking the sequence variant. A nucleic acid construct that includes such sulfotransferase nucleic acid sequences is also described. The SULT1A3 sulfotransferase nucleic acid sequence can encode a sulfotransferase polypeptide including an amino acid sequence variant. SULT1A3 nucleotide sequence variants can be within an intron. For example, introns 4 and 6 each can include an adenine at nucleotide 69. Intron 7 can include a thymine at nucleotide 113. SULT1A3 nucleotide sequence variants can include insertion of nucleotides within intron sequences. The nucleotide sequence 5'-CAGT-3' can be inserted, for example, within intron 3. A SULT1A3 nucleotide sequence variant also can include a guanine at nucleotide 105 of the coding sequence.

The invention also features SULT1A1 and SULT1A2 nucleotide sequence variants. The SULT1A1 nucleotide sequence variants can include, for example, a cytosine at nucleotide 138 of intron 1A or a thymine at nucleotide 34 of intron 5. A SULT1A1 variant also can include, for example, an adenine at nucleotide 57, 110, or 645 of the SULT1A1 coding sequence. The SULT1AL nucleic acid sequence can encode a sulfotransferase polypeptide having, for example, a glutamine at amino acid 37. SULT1A2 nucleotide sequence variants can include a thymine at nucleotide 78 of intron 5 or a thymine at nucleotide 9 of intron 7. The coding sequence of SULT1A2 can include a thymine of nucleotide 550. The SULT1A2 nucleic acid sequence can encode, for example a cysteine at amino acid 184.

In another aspect, the invention features a method for determining a risk estimate of a hormone disease in a patient. The method includes detecting the presence or absence of a sulfotransferase nucleotide sequence variant in a patient, and determining the risk estimate based, at least in part, on presence or absence of the variant in the patient. The hormone dependent disease can be, for example, breast cancer, prostate cancer or ovarian cancer.

The invention also features a method for determining sulfonator status in a subject. The method includes detecting the presence or absence of a sulfotransferase allozyme or nucleotide sequence variant in a subject, and determining the sulfonator status based, at least in part, on said determination.

An antibody having specific binding affinity for a sulfotransferase polypeptide is also described.

The invention also features isolated nucleic acid molecules that include a sulfotransferase nucleic acid sequence that encode a sulfotransferase allozyme. The allozyme can be selected from the group consisting of SULT1A1*4, SULT1A2*4, SULT1A2*5, and SULT1A2*6. Sulfotransferase nucleic acid sequences that include sulfotransferase alleles selected from the group consisting of SULT1A1*1, SULT1A1*2, SULT1A1*3A, SULT1A1*3B and SULT1A1*4 also are featured. In particular, the SULT1A1*1 allele can be SULT1A1*1A to SULT1A1*1K. The SULT1A2 allele can be SULT1A2*1A–1D, SULT1A2*2A–2C, SULT1A2*3A–3C or SULT1A2*4–*6.

The invention also relates to an article of manufacture that includes a substrate and an array of different sulfotransferase nucleic acid molecules immobilized on the substrate. Each of the different sulfotransferase nucleic acid molecules includes a different sulfotransferase nucleotide sequence variant and nucleotides flanking the sequence variant. The array of different sulfotransferase nucleic acid molecules can include at least two nucleotide sequence variants of SULT1A1, SULT1A2, or SULT1A3.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1A is a scattergram that depicts the relationship between TS PST enzymatic activity and thermal stability in 905 human platelet samples. FIG. 1B is a scattergram that correlates human platelet SULT1A1 genotype with TS PST phenotype.

FIG. 5 is the gene sequence of SULT1A1 (SEQ ID NO:29).

Figure 6B:
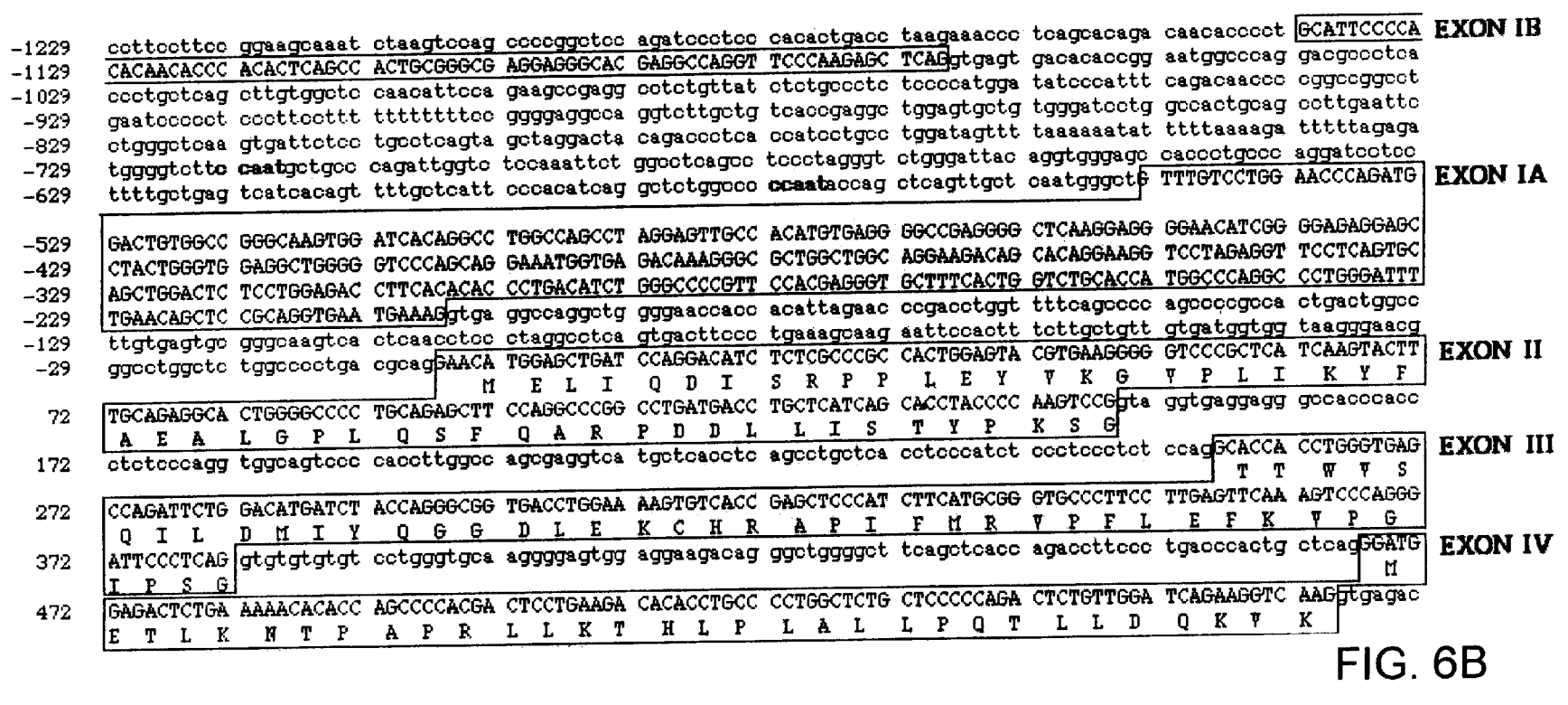
Figure 6C:
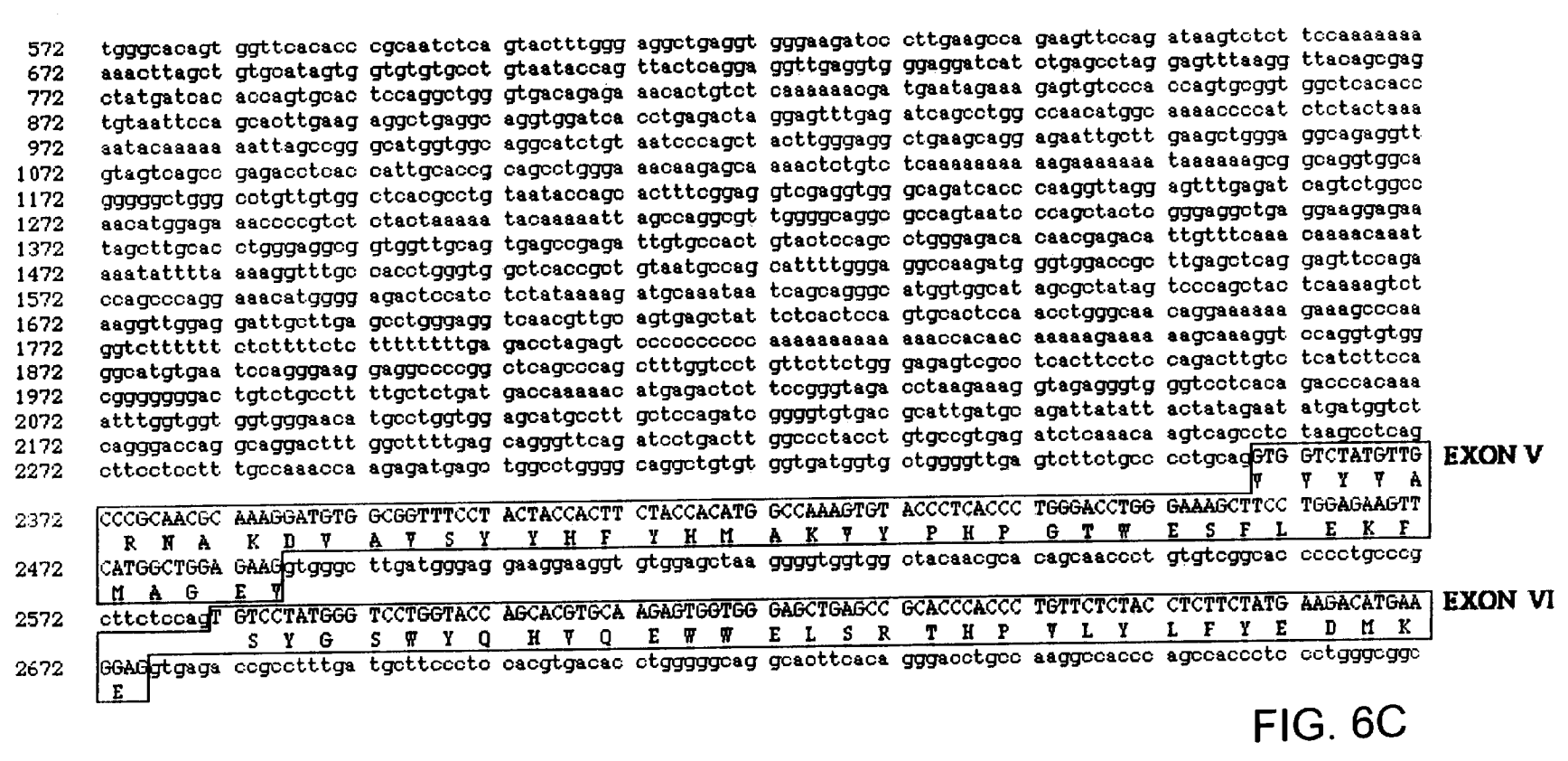

FIG. 6 is the gene sequence of SULT1A2 (SEQ ID NO:31).

FIG. 7 is the gene sequence of SULT1A3 (SEQ ID NO:33).

DETAILED DESCRIPTION

Figure 1A:
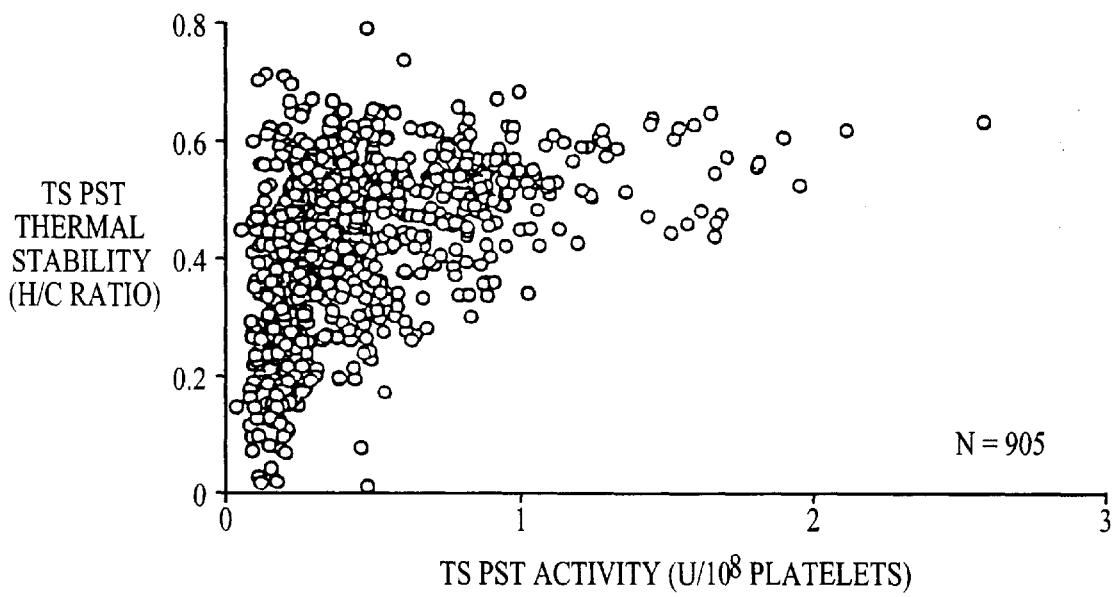
FIGS. 1A and 1B represent human platelet TS PST phenotypes.

The invention features an isolated nucleic acid molecule that includes a sulfotransferase nucleic acid sequence. The sulfotransferase nucleic acid sequence includes a nucleotide sequence variant and nucleotides flanking the sequence variant. As used herein, "isolated nucleic acid" refers to a sequence corresponding to part or all of the sulfotransferase gene, but free of sequences that normally flank one or both sides of the sulfotransferase gene in a mammalian genome. The term "sulfotransferase nucleic acid sequence" refers to a nucleotide sequence of at least about 14 nucleotides in length. For example, the sequence can be about 14 to 20, 20–50, 50–100 or greater than 100 nucleotides in length. Sulfotransferase nucleic acid sequences can be in sense or antisense orientation. Suitable sulfotransferase nucleic acid sequences include SULT1A1, SULT1A2 and SULT1A3 nucleic acid sequences. As used herein, "nucleotide sequence variant" refers to any alteration in the wild-type gene sequence, and includes variations that occur in coding and non-coding regions, including exons, introns, promoters and untranslated regions.

In some instances, the nucleotide sequence variant results in a sulfotransferase polypeptide having an altered amino acid sequence. The term "polypeptide" refers to a chain of at least four amino acid residues. Corresponding sulfotransferase polypeptides, irrespective of length, that differ in amino acid sequence are herein referred to as allozymes. For example, a sulfotransferase nucleic acid sequence can be a SULT1A1 nucleic acid sequence and include an adenine at nucleotide 110. This nucleotide sequence variant encodes a sulfotransferase polypeptide having a glutamine at amino acid residue 37. This polypeptide would be considered an allozyme with respect to a corresponding sulfotransferase polypeptide having an arginine at amino acid residue 37. In addition, the nucleotide variant can include an adenine at nucleotide 638 or a guanine at nucleotide 667, and encode a sulfotransferase polypeptide having a histidine at amino acid residue 213 or a valine at amino acid residue 223, respectively.

As described herein, there are at least four SULT1A1 allozymes. SULT1A1*1 is the most common and contains an arginine at residues 37 and 213, and a methionine at residue 223. SULT1A1*2 contains an arginine at residue 37, a histidine at residue 213 and a methionine at residue 223. SULT1A1*3 contains an arginine at residues 37 and 213, and a valine at residue 223. SULT1A*4 is the least common, and contains a glutamine at residue 37, an arginine at residue 213, and a methionine at residue 223.

The sulfotransferase nucleic acid sequence also can encode SULT1A2 polypeptide variants. Non-limiting examples of SULT1A2 polypeptide variants include an isoleucine at amino acid residue 7, a leucine at amino acid residue 19, a cysteine at amino acid residue 184, or a threonine at amino acid 235. These polypeptide variants are encoded by nucleotide sequence variants having a cytosine at nucleotide 20, a thymine at nucleotide 56, a thymine at nucleotide 50 and a cytosine at nucleotide 704.

There are at least six different SULT1A2 allozymes that differ at residues 7, 19, 184 and 235. For example, SULT1A2*1 contains an isoleucine, a proline, an arginine and an asparagine at residues 7, 19, 184 and 235, respectively, and represents the most common allozyme. SULT1A2*2 differs from SULT1A2*1 in that it contains a threonine at residues 7 and 235. SULT1A2*3 differs from SULT1A2*1 in that it contains a leucine at residue 19. SULT1A2*4 differs from SULT1A2*2 in that it contains a cysteine at residue 184. SULT1A2*5 differs from SULT1A2*1 in that it contains a threonine at residue 7. SULT1A2*6 differs from SULT1A2*1 in that it contains an isoleucine at residue 7.

As described herein, SULT1A1*2 and SULT1A2*2 are associated with decreased TS PST thermal stability in the human liver, but the biochemical and physical properties of recombinant SULT allozymes indicated that the "TS PST phenotype" in the liver is most likely due to expression of SULT1A1. For example, based both on its apparent $K_m$ value for 4-nitrophenol and its $T_{50}$ value, SULT1A1*2 was not consistently associated with low levels of TS PST activity in the liver, but was uniformly associated with decreased levels of platelet TS PST activity and thermal stability. It appears that SULT1A1*2 is associated with lower levels of TS PST activity in tissue from subjects with benign rather than neoplastic disease.

Figure 5B:
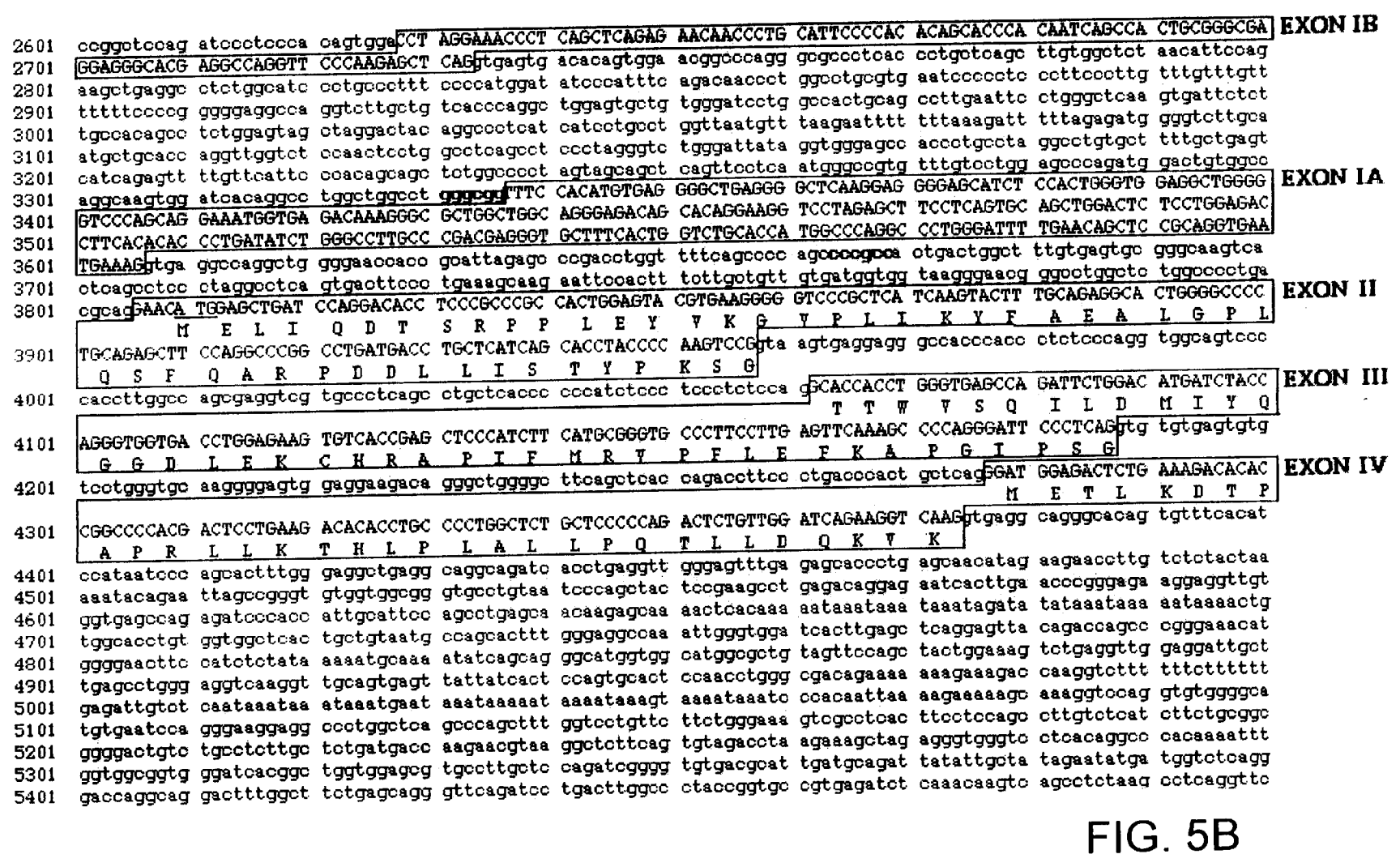
Figure 5C:
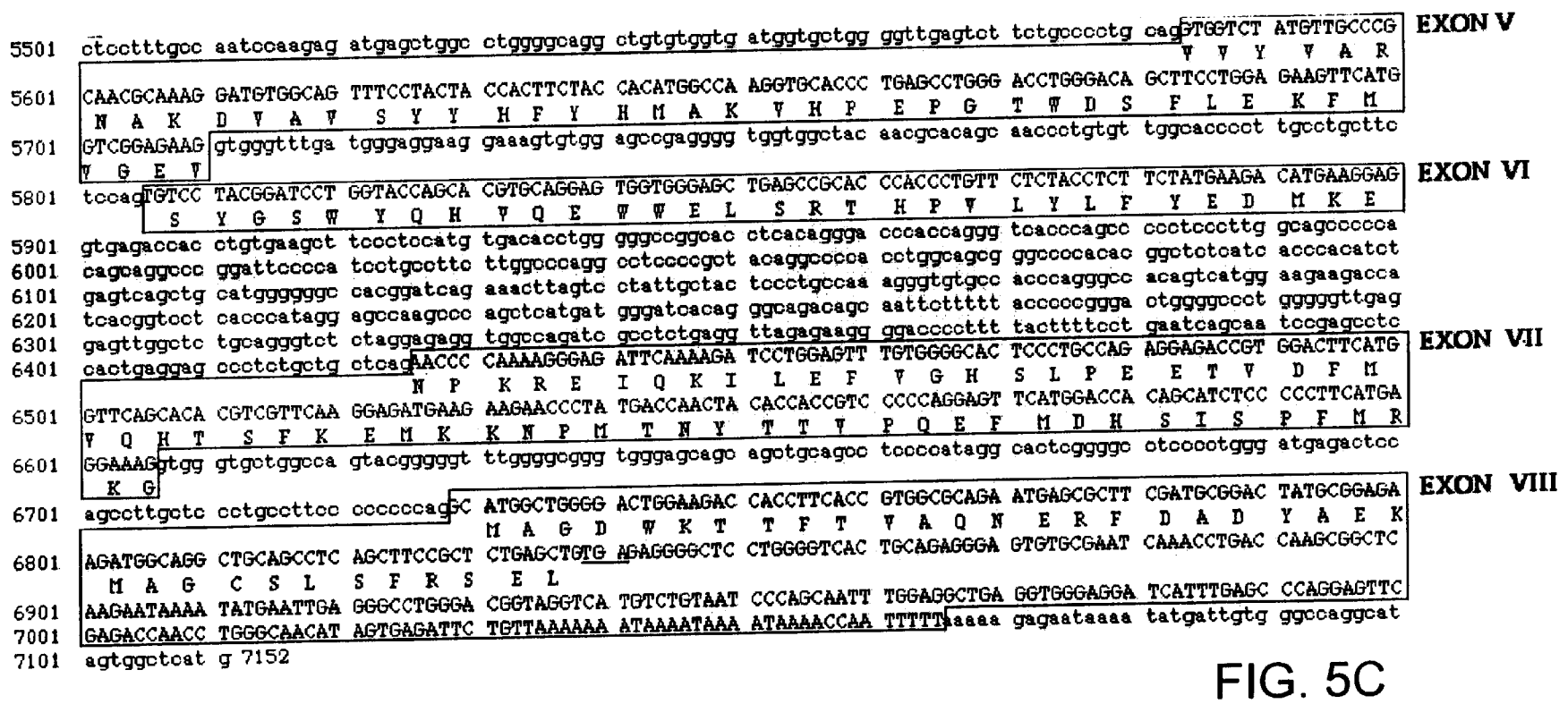

Certain sulfotransferase nucleotide variants do not alter the amino acid sequence. Such variants, however, could alter regulation of transcription as well as mRNA stability. SULT1A1 variants can occur in intron sequences, for example, within intron 1A and introns 5-7 (i.e., intron 5 is immediately after exon 5 in FIG. 5). In particular, the nucleotide sequence variant can include a cytosine at nucleotide 138 of intron 1A, or a thymine at nucleotide 34 or an adenine at nucleotide 35 of intron 5. Intron 6 sequence variants can include a guanine at nucleotide 11, a cytosine at nucleotide 17, an adenine at nucleotide 35, a guanine at nucleotide 45, a guanine at nucleotide 64, a cytosine at nucleotide 488, and an adenine at nucleotide 509. Intron 7 variants can include a thymine at nucleotide 17, a cytosine at nucleotide 69 and a guanine at nucleotide 120. SULT1A1 nucleotide sequence variants that do not change the amino acid sequence also can be within an exon or in the 3' untranslated region. For example, the coding sequence can contain an adenine at nucleotide 57, a cytosine at nucleotide 153, a guanine at nucleotide 162, a cytosine at nucleotide 600, or an adenine at nucleotide 645. The 3' untranslated region can contain a guanine at nucleotide 902 or a thymine at nucleotide 973.

Similarly, certain SULT1A2 and SULT1A3 variants do not alter the amino acid sequence. Such SULT1A2 nucleotide sequence variants can be within an intron sequence, a coding sequence or within the 3' untranslated region. In particular, the nucleotide variant can be within intron 2, 5 or 7. For example, intron 2 can contain a cytosine at nucleotide 34. Intron 5 can include a thymine at nucleotide 78, and intron 7 can include a thymine at nucleotide 9. In addition, a cytosine can be at nucleotide 24 or a thymine at nucleotide 895 in SULT1A2 coding sequence. A guanine can be at nucleotide 902 in the 3' untranslated region. SULT1A3 nucleotide sequences variant can include a guanine at nucleotide 105 of the coding region (within exon 3). In addition, intron 3 of SULT1A3 can include an insertion of nucleotides. For example, the four nucleotides 5'-CAGT-3' can be inserted between nucleotides 83 and 84 of intron 3. Introns 4, 6, and 7 also can contain sequence variants. For example, nucleotide 69 of introns 4 and 6 can contain an adenine. Nucleotide 113 of intron 7 can contain a thymine.

Sulfotransferase allozymes as described above are encoded by a series of sulfotransferase alleles. These alleles represent nucleic acid sequences containing sequence variants, typically multiple sequence variants, within intron, exon and 3' untranslated sequences. Representative examples of single nucleotide variants are described above. Table 3 sets out a series of 13 SULT1A1 alleles (SULT1A1*1A to SULT1A1*1K) that encode SULT1A1*1. SULT1A1*1A to SULT1A1*1K range in frequency from about 0.7% to about 33%, as estimated from random blood donors and hepatic biopsy samples. Two alleles, SULT1A1*3A and SULT1A1*3B each encode SULT1A1*3, and represent about 0.3% to about 1.6% of all SULT1A1 alleles. SULT1A1*2 and SULT1A1*4 are encoded by single alleles, SULT1A1*2 and SULT1A1*4, respectively. SULT1A1*2 represents about 31% of the alleles, whereas SULT1A1*4 accounts for only about 0.3% of the alleles.

Numerous SULT1A2 alleles also exist (Table 2A). For example, SULT1A2*1 is encoded by four alleles (SULT1A2*1A to SULT1A2*1D) that range in frequency from 0.8% to about 47%. SULT1A2*2 and SULT1A2*3 are each encoded by three alleles (*2A–*2C and *3A–*3C). These alleles range in frequency from 0.8% up to about 26%. Single alleles encode SULT1A2*4, SULT1A2*5, and SULT1A2*6, with each representing about 0.8% of the SULT1A2 alleles. As described herein, SULT1A2 alleles are in linkage disequilibrium with the alleles for SULT1A1.

The relatively large number of alleles and allozymes for SULT1A1 and SULT1A2, with three common allozymes for each gene, indicates the potential complexity of SULT pharmacogenetics. Such complexity emphasizes the need for determining single nucleotide variants, as well as complete haplotypes of patients. For example, an article of manufacture that includes a substrate and an array of different sulfotransferase nucleic acid molecules immobilized on the substrate allows complete haplotypes of patients to be assessed. Each of the different sulfotransferase nucleic acid molecules includes a different sulfotransferase nucleotide sequence variant and nucleotides flanking the sequence variant. The array of different sulfotransferase nucleic acid molecules can include at least two nucleotide sequence variants of SULT1A1, SULT1A2, or SULT1A3, or can include all of the nucleotide sequence variants known for each gene.

Suitable substrates for the article of manufacture provide a base for the immobilization of nucleic acid molecules into discrete units. For example, the substrate can be a chip or a membrane. The term "unit" refers to a plurality of nucleic acid molecules containing the same nucleotide sequence variant. Immobilized nucleic acid molecules are typically about 20 nucleotides in length, but can vary from about 14 nucleotides to about 100 nucleotides in length. In practice, a sample of DNA or RNA from a subject can be amplified, hybridized to the article of manufacture, and then hybridization detected. Typically, the amplified product is labeled to facilitate hybridization detection. See, for example, Hacia, J. G. et al., *Nature Genetics*, 14:441–447 (1996); and U.S. Pat. Nos. 5,770,722 and 5,733,729.

As a result of the present invention, it is now possible to determine sulfonator status of a subject. As used herein "sulfonator status" refers to the ability of a subject to transfer a sulfate group to a substrate. A variety of drugs (e.g., acetaminophen), hormones (e.g., estrogen) and neurotransmitters (e.g., dopamine and other phenolic monoamines) are substrates for these enzymes. Generally, sulfonation is considered a detoxification mechanism, as reaction products are more readily excreted. Certain substrates, however, become more reactive upon sulfonation. For example, the N-hydroxy metabolite of 2-acetylaminoflourene is converted to a N—O-sulfate ester, which is reactive with biological macromolecules. Thus, a determination of the presence or absence of nucleotide sequence variants or allozymes facilitates the prediction of therapeutic efficacy and toxicity of drugs on an individual basis, as well as the ability to biotransform certain hormones and neurotransmitters. In addition, the ability to sulfonate hormones may play a role in cancer.

The presence or absence of sulfotransferase variants allows the determination of a risk estimate for the development of a hormone dependent disease. As used herein, "hormone dependent disease" refers to a disease in which a hormone plays a role in the pathophysiology of the disease. Non-limiting examples of hormone dependent diseases include breast cancer, ovarian cancer, and prostate cancer. Risk estimate indicates the relative risk a subject has for developing a hormone dependent disease. For example, a risk estimate for development of breast cancer can be determined based on the presence or absence of sulfotransferase variants. A subject containing, for example, the SULT1A1*2, of sulfotransferase variant may have a greater likelihood of having breast cancer. Additional risk factors include, for example, family history of breast cancer and other genetic factors such as mutations within the BRCA1 and BRCA2 genes.

Sulfotransferase nucleotide sequence variants can be assessed, for example, by sequencing exons and introns of the sulfotransferase genes, by performing allele-specific hybridization, allele-specific restriction digests, mutation specific polymerase chain reactions (MSPCR), or by single-stranded conformational polymorphism (SSCP) detection. Polymerase chain reaction (PCR) refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, R. *Genetic Engineering News*, 12(9):1 (1992); Guatelli et al., *Proc. Natl. Acad. Sci. USA*, 87:1874–1878 (1990); and Weiss, R., *Science*, 254:1292 (1991).

Genomic DNA is generally used in the analysis of sulfotransferase nucleotide sequence variants. Genomic DNA is typically extracted from peripheral blood samples, but can be extracted from such tissues as mucosal scrapings of the lining of the mouth or from renal or hepatic tissue. Routine methods can be used to extract genomic DNA from a blood or tissue sample, including, for example, phenol extraction. Alternatively, genomic DNA can be extracted with kits such as the QIAamp® Tissue Kit (Qiagen, Chatsworth, Calif.), Wizard® Genomic DNA purification kit (Promega, Madison, Wis.) and the A.S.A.P.™ Genomic DNA isolation kit (Boehringer Mannheim, Indianapolis, Ind.).

For example, exons and introns of the sulfotransferase gene can be amplified through PCR and then directly sequenced. This method can be varied, including using dye primer sequencing to increase the accuracy of detecting heterozygous samples. Alternatively, a nucleic acid molecule can be selectively hybridized to the PCR product to detect a gene variant. Hybridization conditions are selected such that the nucleic acid molecule can specifically bind the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate/0.1% sodium dodecyl sulfate (SDS) and washed in 0.1×SSC (0.015M NaCl/0.0015 M sodium citrate), 0.1% SDS at 65° C. Hybridization conditions can be adjusted to account for unique features of the nucleic acid molecule, including length and sequence composition.

Allele-specific restriction digests can be performed in the following manner. For example, if a nucleotide sequence variant introduces a restriction site, restriction digest with the particular restriction enzyme can differentiate the alleles. For SULT1 variants that do not alter a common restriction site, primers can be designed that introduce a restriction site when the variant allele is present, or when the wild-type allele is present. For example, the SULT1A*2 allele does not have an altered restriction site. A KasI site can be introduced in all SULT1A1 alleles, except SULT1A*2, using a mutagenic primer (e.g., 5' CCA CGG TCT CCT CTG GCA GGG GG 3', SEQ ID NO:1). A portion of SULT1A1 alleles can be amplified using the mutagenic primer and a primer having, for example, the nucleotide sequence of 5' GTT GAG GAG TTG GCT CTG CAG GGT C 3' (SEQ ID NO:2). A KasI digest of SULT1A1 alleles, other than SULT1A*2, yield restriction products of about 173 base pairs (bp) and about 25 bp. In contrast, the SULT1A*2 allele is not cleaved, and thus yields a restriction product of about 198 bp.

The SULT1A2*2 allele can be detected using a similar strategy. For example, an additional StyI site can be introduced in the SULT1A2*2 allele using the mutagenic primer 5' CAC GTA CTC CAG TGG CGG GCC CTA G 3' (SEQ ID NO:3). Upon amplification of a portion of the SULT1A2 alleles using the mutagenic primer and a primer having the nucleotide sequence of 5' GGA ACC ACC ACA TTA GAA C 3' (SEQ ID NO:4), a StyI digest yields restriction products of 89 bp, 119 bp and 25 bp for SULT1A2*2. The other SULT1A2 alleles described herein yield restriction products of 89 bp and 144 bp.

Certain variants, such as the insertion within intron 3 of the SULT1A3 gene discussed above, change the size of the DNA fragment encompassing the variant. The insertion of nucleotides can be assessed by amplifying the region encompassing the variant and determining the size of the amplified products in comparison with size standards. For example, the intron 3 region of the SULT1A3 gene can be amplified using a primer set from either side of the variant. One of the primers is typically labeled, for example, with a fluorescent moiety, to facilitate sizing. The amplified products can be electrophoresed through acrylamide gels using a set of size standards that are labeled with a fluorescent moiety that differs from the primer.

PCR conditions and primers can be developed that amplify a product only when the variant allele is present or only when the wild-type allele is present (MSPCR or allele-specific PCR). For example, patient DNA and a control can be amplified separately using either a wild-type primer or a primer specific for the variant allele. Each set of reactions is then examined for the presence of amplification products using standard methods to visualize the DNA. For example, the reactions can be electrophoresed through an agarose gel and DNA visualized by staining with ethidium bromide or other DNA intercalating dye. In DNA samples from heterozygous patients, reaction products would be detected in each reaction. Patient samples containing solely the wild-type allele would have amplification products only in the reaction using the wild-type primer. Similarly, patient samples containing solely the variant allele would have amplification products only in the reaction using the variant primer.

Mismatch cleavage methods also can be used to detect differing sequences by PCR amplification, followed by hybridization with the wild-type sequence and cleavage at points of mismatch. Chemical reagents, such as carbodiimide or hydroxylamine and osmium tetroxide can be used to modify mismatched nucleotides to facilitate cleavage.

Alternatively, sulfotransferase nucleotide sequence variants can be detected by antibodies that have specific binding affinity for variant sulfotransferase polypeptides. Variant sulfotransferase polypeptides can be produced in various ways, including recombinantly. The genomic nucleic acid sequences of SULT1A1, SULT1A2 and SULT1A3 have GenBank accession numbers of U52852, U34804 and U20499, respectively. Amino acid changes can be introduced by standard techniques including oligonucleotide-directed mutagenesis and site-directed mutagenesis through PCR. See, *Short Protocols in Molecular Biology*, Chapter 8, Green Publishing Associates and John Wiley & Sons, Edited by Ausubel, F. M et al., 1992.

A nucleic acid sequence encoding a sulfotransferase variant polypeptide can be ligated into an expression vector and used to transform a bacterial or eukaryotic host cell. In general, nucleic acid constructs include a regulatory sequence operably linked to a sulfotransferase nucleic acid sequence. Regulatory sequences do not typically encode a gene product, but instead affect the expression of the nucleic acid sequence. In bacterial systems, a strain of *Escherichia coli* such as BL-21 can be used. Suitable *E. coli* vectors include the pGEX series of vectors that produce fusion proteins with glutathione S-transferase (GST). Transformed *E. coli* are typically grown exponentially, then stimulated with isopropylthiogalactopyranoside (IPTG) prior to harvesting. In general, such fusion proteins are soluble and can be purified easily from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In eukaryotic host cells, a number of viral-based expression systems can be utilized to express sulfotransferase variant polypeptides. A nucleic acid encoding a sulfotransferase variant polypeptide can be cloned into, for example, a baculoviral vector and then used to transfect insect cells. Alternatively, the nucleic acid encoding a sulfotransferase variant can be introduced into a SV40, retroviral or vaccinia based viral vector and used to infect host cells.

Mammalian cell lines that stably express sulfotransferase variant polypeptides can be produced by using expression vectors with the appropriate control elements and a selectable marker. For example, the eukaryotic expression vector pCR3.1 (Invitrogen, San Diego, Calif.) is suitable for expression of sulfotransferase variant polypeptides in, for example, COS cells. Following introduction of the expression vector by electroporation, DEAE dextran, or other suitable method, stable cell lines are selected. Alternatively, amplified sequences can be ligated into a mammalian expression vector such as pcDNA3 (Invitrogen, San Diego, Calif.) and then transcribed and translated in vitro using wheat germ extract or rabbit reticulocyte lysate.

Sulfotransferase variant polypeptides can be purified by known chromatographic methods including DEAE ion exchange, gel filtration and hydroxylapatite chromatography. Van Loon, J. A. and R. M. Weinshilboum, *Drug Metab. Dispos.*, 18:632–638 (1990); Van Loon, J. A. et al., *Biochem. Pharmacol.*, 44:775–785 (1992).

Various host animals can be immunized by injection of a sulfotransferase variant polypeptide. Host animals include rabbits, chickens, mice, guinea pigs and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin and dinitrophenol. Polyclonal antibodies are heterogenous populations of antibody molecules that are contained in the sera of the immunized animals. Monoclonal antibodies, which are homogeneous populations of antibodies to a particular antigen, can be prepared using a sulfotransferase variant polypeptide and standard hybridoma technology. In particular, monoclonal antibodies can be obtained by any technique that provides for the production of antibody molecules by continuous cell lines in culture such as described by Kohler, G. et al., *Nature*, 256:495 (1975), the human B-cell hybridoma technique (Kosbor et al., *Immunology Today*, 4:72 (1983); Cole et al., *Proc. Natl. Acad. Sci USA*, 80:2026 (1983)), and the EBV-hybridoma technique (Cole et al., "Monoclonal Antibodies and Cancer Therapy", Alan R. Liss, Inc., pp. 77–96 (1983). Such antibodies can be of any immunoglobulin class including IgG, IgM, IgE, IgA, IgD and any subclass thereof. The hybridoma producing the monoclonal antibodies of the invention can be cultivated in vitro and in vivo.

Antibody fragments that have specific binding affinity for a sulfotransferase variant polypeptide can be generated by known techniques. For example, such fragments include but are not limited to F(ab')$_2$ fragments that can be produced by pepsin digestion of the antibody molecule, and Fab fragments that can be generated by reducing the disulfide bridges of F(ab')$_2$ fragments. Alternatively, Fab expression libraries can be constructed. See, for example, Huse et al., *Science*, 246:1275 (1989). Once produced, antibodies or fragments thereof are tested for recognition of sulfotransferase variant polypeptides by standard immunoassay methods including ELISA techniques, radioimmunoassays and Western blotting. See, *Short Protocols in Molecular Biology*, Chapter 11, Green Publishing Associates and John Wiley & Sons, Edited by Ausubel, F. M et al., 1992.

The invention will be further described in the following examples, which do not limit the scope of the invention described in the claims.

EXAMPLES 1.0 Methods and Materials 1.1 Tissue Samples

Human hepatic "surgical waste" tissue was obtained from 61 patients undergoing clinically-indicated hepatectomies or open hepatic biopsies and was stored at −80° C. These frozen hepatic tissue samples were homogenized in 5 mM potassium phosphate buffer, pH 6.5, and centrifuged at 100,000×g for 1 hr to obtain high-speed supernatant (HSS) cytosolic preparations. Campbell, N. R. C. et al., *Biochem. Pharmacol.*, 36:1435–1446 (1987). Platelet samples were obtained from blood samples from 905 members of 134 randomly selected families at the Mayo Clinic in Rochester, Minn. All tissue samples were obtained under guidelines approved by the Mayo Clinic Institutional Review Board.

1.2 PST Enzyme Activity, Thermal Stability and Inhibitor Sensitivity

TS PST enzyme activity was measured with an assay that involves the sulfate conjugation of substrate, in this case 4-nitrophenol, in the presence of [$^{35}$S]-3'-phosphoadenosine-5'-phosphosulfate (PAPS), the sulfate donor for the reaction. See, Campbell, N. R. C. et al., *Biochem. Pharmacol.*, 36:1435–1446 (1987). Blanks were samples that did not contain sulfate acceptor substrate. Unless otherwise stated, concentrations of 4-nitrophenol and PAPS were 4 μM and 0.4 μM, respectively. Substrate kinetic experiments were conducted in the presence of a series of concentrations of 4-nitrophenol and PAPS to make it possible to calculate apparent $K_m$ values. Enzyme activity was expressed as nmoles of sulfate conjugated product formed per hr of incubation. Protein concentrations were measured by the dye-binding method of Bradford with bovine serum albumin (BSA) as a standard.

Enzyme thermal stability was determined as described by Reiter and Weinshilboum, *Clin. Pharmacol. Ther.*, 32:612–621 (1982). Specifically, hepatic HSS preparations or platelet preparations were thawed, diluted and were then either subjected to thermal inactivation for 15 min at 44° C. or were kept on ice as a control. In these experiments, heated over control (H/C) ratios were used as a measure of thermal stability. The thermal stability of recombinant proteins was measured by incubating diluted, transfected COS-1 cell HSS for 15 min in a Perkin Elmer 2400 thermal cycler at a series of temperatures. All samples were placed on ice immediately after the thermal inactivation step, and PST activity was measured in both heated and control samples. Thermal inactivation curves were then constructed for each recombinant protein by plotting SULT activity expressed as a percentage of the control value. The concentration of 4-nitrophenol used to assay each of the recombinant proteins was determined on the basis of the results of the substrate kinetic experiments during which apparent $K_m$ values had been determined. Those concentrations were: SULT1A1 (*1, *2, *3), 4 μM; SULT1A2, 100 μM; SULT1A2*2, 3 mM; SULT1A2*3, 50 μM; and SULT1A3, 3 mM.

DCNP inhibition was determined by measuring enzyme activity in the presence of a series of DCNP concentrations dissolved in dimethylsulfoxide. Blank samples for those experiments contained the appropriate concentration of DCNP, but no sulfate acceptor substrate. The concentration of 4-nitrophenol used to study each recombinant protein was the same as was used in the thermal stability experiments. All assays for the determination of apparent $K_m$ values, thermal stability or DCNP inhibition were performed in triplicate, and all experiments were performed at least three times, i.e., each of the data points shown subsequently represents the average of at least nine separate assays.

1.3 PCR Amplification and DNA Sequencing

Figure 2:
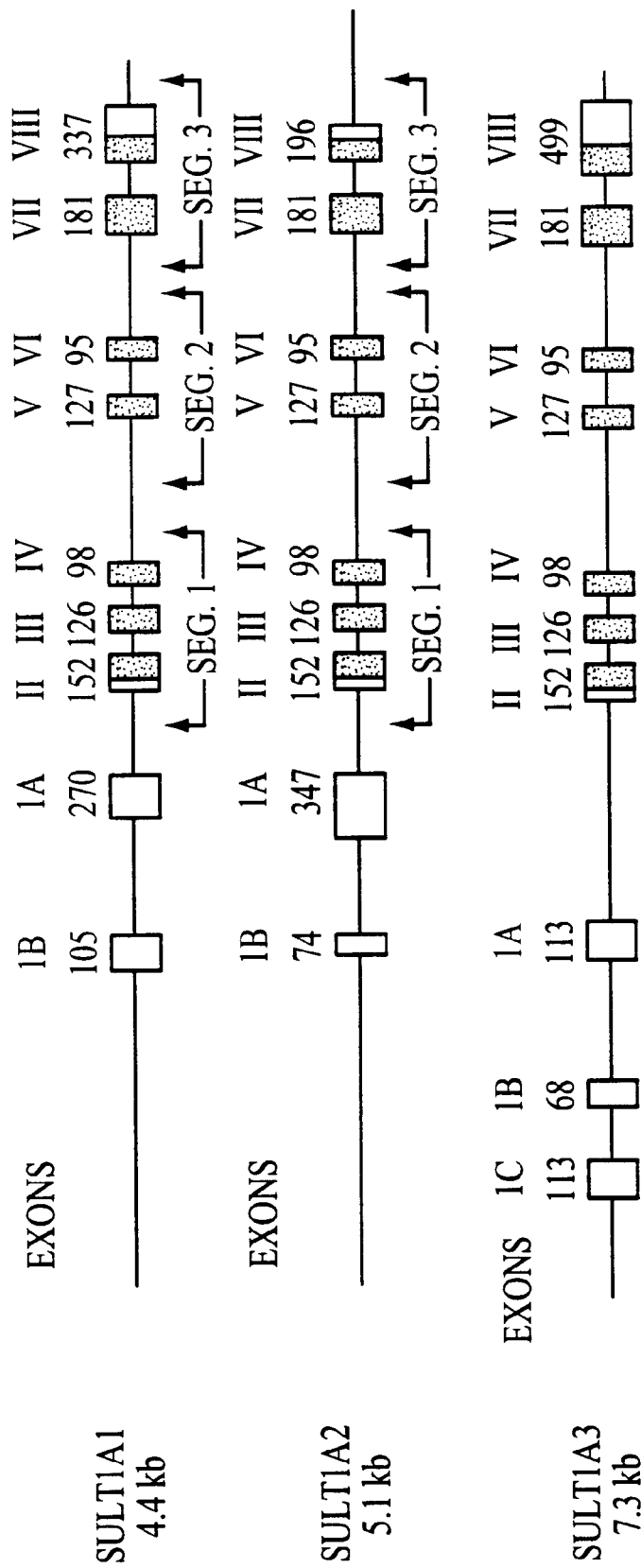
FIG. 2 is a representation of human SULT1A1, SULT1A2, and SULT1A3 gene structures and the PCR strategy used to amplify the open reading frame (ORF) of each gene in three segments. Black rectangles represent exons that encode cDNA ORF sequence, while open rectangles represent exon or portions of exons that encode cDNA untranslated region (UTR) sequence. Roman numerals are exon numbers, and arabic numerals are exon lengths in bp. Gene lengths in kb from initial to final exons are also indicated. Forward and reverse arrows indicate the placement within introns of the PCR primers used to amplify, in three separate reactions, the ORFs of SULT1A1 and SULT1A2.
Figure 3:
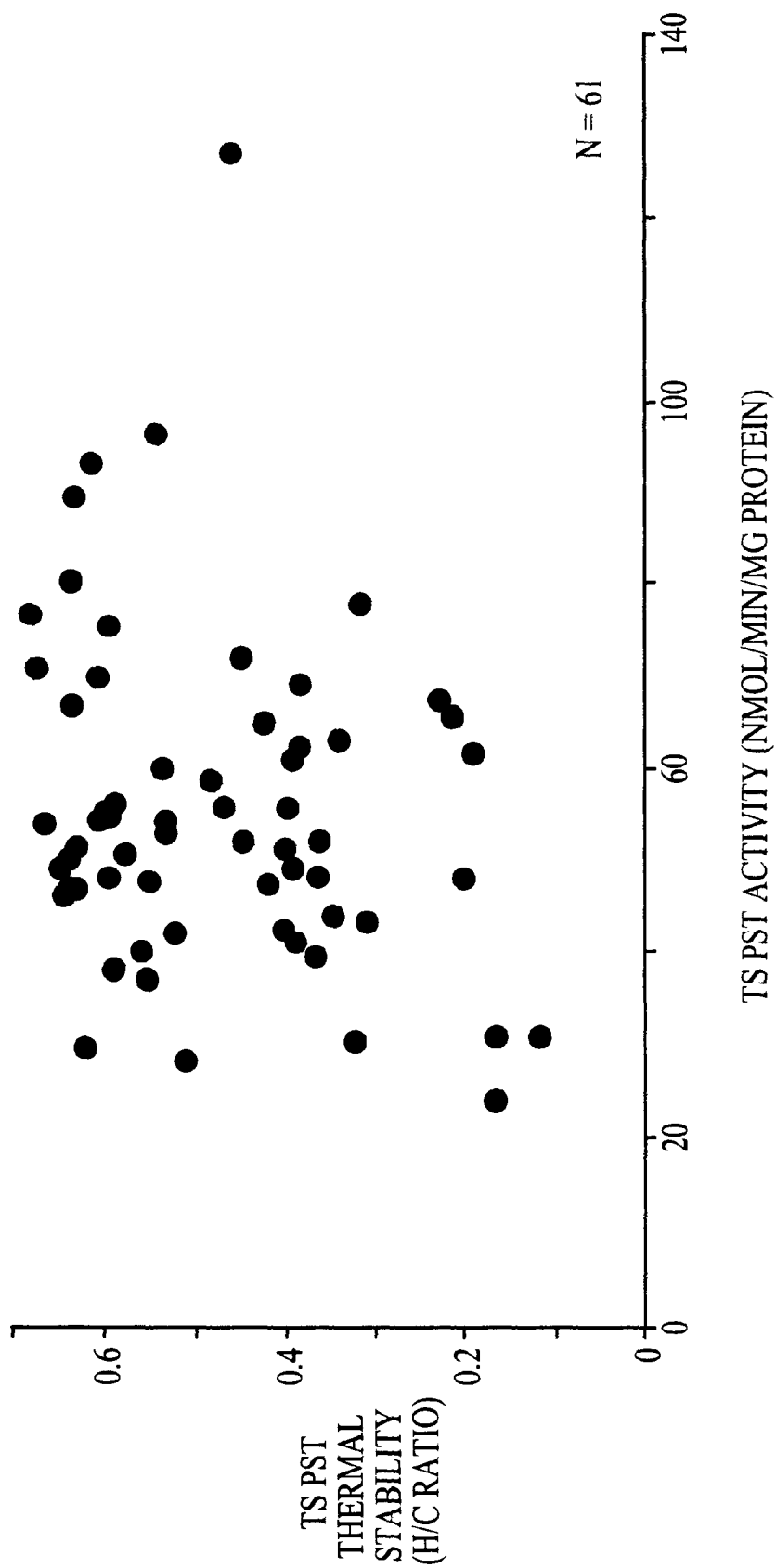
FIG. 3 is a scattergram that depicts the relationship between TS PST enzymatic activity and thermal stability in 61 human liver biopsy samples.

Total genomic DNA was isolated from the human liver biopsy samples with a QIAamp Tissue Kit (Qiagen, Inc., Chatsworth, Calif.). In addition, genomic DNA was isolated from 150 randomly selected Caucasian blood donors at the Mayo Clinic Blood Blank. Gene-specific primers for the PCR were designed by comparing the sequences of SULT1A1, SULT1A2, and SULT1A3 (Genbank accession numbers U52852, U34804 and U20499, respectively) and identifying intron sequences that differed among the three genes. These gene-specific primers were then used to amplify, in three separate segments for each gene, the coding regions of either SULT1A1 or SULT1A2 (FIG. 2). To assure specificity, an initial long PCR amplification was performed using oligonucleotide primers that annealed to unique sequences present in the 5'-and 3'-flanking regions of each gene. Those long PCR products were then used as templates for the subsequent PCR reactions to amplify coding regions of the genes. Sequences of the PCR primers used to perform these experiments are listed in Table 1. In Table 1, "I" represents "intron", "F" represents "forward", "R" represents "reverse" and "D" ("downstream") represents 3'-flanking region of the gene.

DNA sequencing was performed with single-stranded DNA as template to help assure the detection of heterozygous samples. To make that possible, single-stranded DNA was generated by exonuclease digestion of either the sense or antisense strand of the double-stranded PCR amplification products. Phosphorothioate groups were conjugated to the 5'-end of either the forward or reverse PCR primer, depending on which of the two strands was to be protected from exonuclease digestion. Specifically, the PCR amplification of gene segments was performed in a 50 μl reaction mixture using Amplitaq Gold DNA polymerase (Perkin Elmer). Digestion of the non-phosphorothioated strand involved incubation of 16 μl of the post-amplification reaction mixture with 20 units of T7 gene 6 exonuclease (United States Biochemical, Cleveland, Ohio) in 10 mM Tris-HCl buffer, pH 7.5, containing 200 μM DTT and 20 μg/ml BSA. This mixture was incubated at 37° C. for 4 hr, followed by inactivation of the exonuclease by incubation at 80° C. for 15 min. The resulting single stranded DNA was used as a sequencing template after PCR primers and salts had been removed with a Microcon-100 microconcentrator (Amicon, Beverly, Mass.). DNA sequencing was performed in the Mayo Clinic Molecular Biology Core Facility with an ABI Model 377 sequencer (Perkin Elmer, Foster City, Calif.) using dye terminator cycler sequencing chemistry.

TABLE 1

PCR Primers

| REACTION | PRIMER | Seq ID | PRIMER SEQUENCE (5' to 3') |
|---|---|---|---|
| SULT1A1 Gene-Specific Amplifications | | | |
| Long PCR | 1AF(−119) | 5 | CCTGGAGACCTTCACACACCCTGATA |
| | DR3296 | 6 | CCACTCTGCCTGGCCCACAATCATA |

TABLE 1-continued

PCR Primers

| REACTION | PRIMER | Seq ID | PRIMER SEQUENCE (5' to 3') |
|---|---|---|---|
| Segment 1 | I1AF11 | 7 | GCTGGGGAACCACCGCATTAGAG |
|  | I4R83 | 8 | AACTCCCAACCTCACGTGATCTG |
| Segment 2 | I4F1018 | 9 | CCTCAGGTTCCTCCTTTGCCAAT |
|  | I6R93 | 10 | TGCCAAGGGAGGGGGCTGGGTGA |
| Segment 3 | I6F395 | 11 | GTTGAGGAGTTGGCTCTGCAGGGTC |
|  | DR3296 | 12 | CCACTCTGCCTGGCCCACAATCATA |
| SULT1A2 Gene-Specific Amplifications | | | |
| Long PCR | IAF(-90) | 13 | GGGCCCCGTTCCACGAGGGTGCTTTCAC |
|  | DR4590 | 14 | TGACCCCACTAGGAAGGGAGTCAGCACCCCTACT |
| Segment 1 | I1AF16 | 15 | GGAACCACCACATTAGAAC |
|  | I4R86 | 16 | TGGAACTTCTGGCTTCAAGGGATCT |
| Segment 2 | I4F1117 | 17 | CCTCAGCTTCCTCCTTTGCCAAA |
|  | I6R81 | 18 | TGGCTGGGTGGCCTTGGC |
| Segment 3 | I6F688 | 19 | GCTGGCTCTATGGGTTTTGAAGT |
|  | DR4094 | 20 | CTGGAGCGGGGAGGTGGCCGTATT |
| SULT1A3 Gene-Specific Amplifications | | | |
| Long PCR | TL F2 | 21 | AATGCCCGCAACAGTGCCTGCTGCATAGAG |
|  | TL R3 | 22 | ACGCTGCCCGGCGGACTCGACGTCCTCCACCATCTT |
| Segment 1 | I1AF1329 | 23 | GAGAATCCCACTTTCTTGCTGTT |
|  | I4R171 | 24 | GGGAACAGTCTATGCCACCATAC |
| Segment 2 | I4F1308 | 25 | GGTTCCTCCTTTGCCAGTTCAAC |
|  | I6R240 | 26 | GGACTAAGTATCTGATCCGTGG |
| Segment 3 | I6F405 | 27 | GGGCCCCAGGGGTTGAGGCTCTT |
|  | DR3666 | 28 | ATATGTGGCCCCACCGGGCATTC |

1.4 COS-1 Cell Expression

Seven different SULT expression constructs were used to transfect COS-1 cells. These constructs included cDNA sequences for all of the common SULT1A1 and 1A2 allozymes observed during the present experiments, 1A1*1, 1A1*2, 1A1*3, 1A2*1, 1A2*2, and 1A2*3, as well as SULT1A3. As a control, transfection was also performed with expression vector that lacked an insert. All SULT cDNA sequences used to create the expression constructs had either been cloned in our laboratory (SULT1A1*2, SULT1A2 2, SULT1A3), were obtained from the Expressed Sequence Tag (EST) database and American Type Culture Collection (SULT1A1*3, SULT1A2*1) or were created by site directed mutagenesis (SULT1A1*1, SULT1A2*3). Each SULT cDNA was then amplified with the PCR and was subcloned into the eukaryotic expression vector pCR3.1 (Invitrogen, San Diego, Calif.). All inserts were sequenced after subcloning to assure that no variant sequence had been introduced during the PCR amplifications. COS-1 cells were then transfected with these expression constructs by use of the DEAE-dextran method. After 48 hr in culture, the transfected cells were harvested and cytosols were prepared as described by Wood, T. C. et al., *Biochem. Biophys. Res. Commun.*, 198:1119–1127 (1994). Aliquots of these cytosol preparations were stored at −80° C. prior to assay.

1.5 Data Analysis

Apparent $K_m$ values were calculated by using the method of Wilkinson with a computer program written by Cleland. Wilkinson, G. N., *Biochem. J.*, 80:324–332 (1961); and Cleland, W. W., *Nature*, 198:463–365 (1963). $IC_{50}$ values and 50% thermal inactivation ($T_{50}$) values were calculated with the GraphPAD InPlot program (GraphPAD InPlot Software, San Diego, Calif.). Statistical comparisons of data were performed by ANOVA with the StatView program, version 4.5 (Abacus Concepts, Inc., Berkeley, Calif.). Linkage analysis was performed using the EH program developed by Terwilliger and Ott, *Handbook of Human Genetic Linkage*, The Johns Hopkins University Press, Baltimore, pp. 188–193 (1994).

2.0

The experiments were performed in an attempt to identify common variant alleles for SULT1A1 and SULT1A2, to determine the biochemical and physical properties of allozymes encoded by common alleles for SULT1A2 and SULT1A1 and to determine whether those alleles might by systematically associated with variation in TS PST phenotype in an important drug-metabolizing organ, the human liver. To achieve these goals, a stepwise strategy was utilized that took advantage of the availability of a "bank" of human hepatic biopsy samples which could be phenotyped for level of TS PST activity and thermal stability. DNA sequence information was available for each of the three known human PST genes (SULT1A1, SULT1A2 and SULT1A3). SULT1A1 and SULT1A2 are located in close proximity within a 50 kb region on human chromosome 16. Raftogianis, R. et al., *Pharmacogenetics*, 6:473–487 (1996).

All exons for both SULT1A1 and SULT1A2 were sequenced using DNA from 150 platelet samples and 61 hepatic tissue samples to detect nucleotide polymorphisms and to determine whether there were significant correlations between genotypes for SULT1A2 and/or SULT1A1 and TS PST phenotype.

2.1 SULT1A2 and SULT1A1 Genetic Polymorphisms

All exons encoding protein for both SULT1A2 and SULT1A1 were PCR amplified in three segments (FIG. 2), and were then sequenced on both strands. Approximately 2 kb of DNA was sequenced for each gene. Therefore, a total of approximately 300 kB and 250 kB of sequence was analyzed for the 150 platelet samples and 61 hepatic biopsy samples, respectively. Thirteen different SULT1A2 alleles were observed among the 122 alleles sequenced in the 61 biopsy samples. These alleles resulted from various combinations of ten different single nucleotide polymorphisms (SNPs) (Table 2A). In Table 2A, numbers at the top indicate the nucleotide position within the ORF, in which 1=the "A" in the "ATG" start codon; or introns, in which an "I" followed by a numeral indicates the location of the nucleotide within the intron (i.e., 12–34 is the 34th nucleotide from the 5'-end of intron 2). Nucleotides shown as white type against a black background alter the encoded amino acid. Nucleotides 895 and 902 lie within the 3'-UTR of the SULT1A2 mRNA. The values shown in the right-hand column indicate allele frequencies in the 61 hepatic biopsy samples.

Four of the SULT1A2 SNPs altered the encoded amino acid, resulting in six different SULT1A2 allozymes, three of which appeared to be "common" (frequency≧1%, Table 2B). In Table 2B, numbers at the top indicate amino acid position from the N-terminus. The right-hand column indicates allozyme frequencies in the 61 hepatic biopsy samples studies. The other three alleles were observed only once, but their existence was confirmed by independent PCR and sequencing reactions. The allele nomenclature used here assigns different numerals after the * to alleles that encode different allozymes, with a subsequent alphabetic designation for alleles that also differ with regard to "silent" SNPs. Since population data was obtained, numeric assignments were not made randomly, but rather could be assigned on the basis of relative allele frequency in the population sample studied, i.e., *1 was more frequent than *2, *2 was more common than was *3, etc.

TABLE 2B

SULT1A2 ALLOZYMES

| Allozyme | Amino Acid | | | | Allozyme Frequency 61 Hepatic Biopsy Samples |
|---|---|---|---|---|---|
| | 7 | 19 | 184 | 235 | |
| *1 | Ile | Pro | Arg | Asn | 0.508 |
| *2 | Thr | Pro | Arg | Thr | 0.287 |
| *3 | Ile | Leu | Arg | Asn | 0.180 |
| *4 | Thr | Pro | Cys | Thr | 0.008 |
| *5 | Thr | Pro | Arg | Asn | 0.008 |
| *6 | Ile | Pro | Arg | Thr | 0.008 |

Thirteen different SULT1A1 alleles were detected in the platelet samples. These alleles encoded four different allozymes for SULT1A1 (Table 3). In Table 3, numbers at the top indicate the nucleotide position within the ORF, in which 1=the "A" in the "ATG" start codon; or introns, in which an "I" followed by a numeral indicates the intron number, and the number after the dash indicates the location of the nucleotide within the intron (i.e., 15–34 is the 34th nucleotide from the 5'-end of the 5th intron). Nucleotides 902 and 973 lie within the 3'-UTR of the SULT1A1 mRNA. The values in the right-hand columns indicate allele frequencies in the 61 hepatic biopsy samples studied or in DNA from 150 randomly selected Caucasian blood donors.

The 61 liver samples contained 10 of the 13 SULT1A1 alleles identified in platelets, and encoded three of the four SULT1A1 allozymes. Alleles SULT1A1*1G, *1H, *1I, *3A and *4 were not present in these liver samples, but two novel SULT1A1 alleles, *1J and *1K, were detected, bringing the total number of SULT1A1 alleles identified to fifteen. These fifteen alleles involve various permutations of 24 individual SNPs located within the approximately 2 kb of SULT1A1 DNA sequenced (Table 4).

TABLE 2A

SULT1A2 ALLELES

| | Exon II | | | | | Exon VI | Exon VII | | Exon VIII | | Allozyme Frequency 61 Hepatic Biopsy Samples |
|---|---|---|---|---|---|---|---|---|---|---|---|
| | 20 | 24 | 56 | I2-34 | I5-78 | 506 | 704 | I7-9 | 895 | 902 | |
| *1A | T | T | C | T | T | C | A | C | T | A | 0.467 |
| *1B | T | T | C | T | C | C | A | C | T | A | 0.025 |
| *1C | T | T | C | C | C | C | A | C | T | A | 0.008 |
| *1D | T | T | C | T | C | C | A | C | C | A | 0.008 |
| *2A | C | C | C | C | C | C | C | C | C | G | 0.262 |
| *2B | C | C | C | T | C | C | C | C | C | G | 0.016 |
| *2C | C | C | C | C | C | C | C | T | C | G | 0.008 |
| *3A | T | T | T | T | C | C | A | C | T | A | 0.156 |
| *3B | T | T | T | T | T | C | A | C | T | A | 0.016 |
| *3C | T | T | T | T | C | C | A | T | T | A | 0.008 |
| *4 | C | C | C | C | C | T | C | C | C | G | 0.008 |
| *5 | C | C | C | C | C | C | A | C | C | G | 0.008 |
| *6 | T | T | C | T | T | C | C | C | C | G | 0.008 |

TABLE 3

SULT1A1 SNP
SULT1A1 ALLELES

| Allele | I1A-138 | Exon II 57 | Exon II 110 | Exon III 153 | Exon III 162 | I5-34 | I5-35 | I6-11 | I6-14 | I6-17 | I6-35 | I6-45 | I6-64 | I6-488 |
|---|---|---|---|---|---|---|---|---|---|---|---|---|---|---|
| *1A | T | G | G | T | A | C | G | C | T | A | A | C | A | T |
| *1B | T | G | G | T | A | C | A | G | C | T | T | A | G | T |
| *1C | T | A | G | C | G | C | G | C | T | A | A | C | A | C |
| *1D | C | G | G | T | A | C | G | C | T | A | A | C | A | T |
| *1E | T | G | G | T | A | C | A | G | C | T | T | A | G | T |
| *1F | C | G | G | T | A | C | A | G | C | T | T | A | G | T |
| *1G | T | G | G | T | A | C | G | G | C | T | T | A | G | T |
| *1H | T | A | G | C | G | C | G | C | T | A | A | C | A | T |
| *1I | T | A | G | T | A | C | G | C | T | A | A | C | A | T |
| *1J | T | A | G | C | G | C | G | C | T | A | A | C | A | C |
| *1K | T | G | G | C | G | C | G | C | T | A | A | C | A | C |
| *2 | T | G | G | C | G | C | G | C | T | A | A | C | A | C |
| *3A | T | G | G | T | A | C | G | C | T | A | A | C | A | T |
| *3B | T | G | G | T | A | T | A | G | C | T | T | A | G | T |
| *4 | T | A | A | T | A | C | A | G | C | T | T | A | G | T |

| Allele | I6-509 | Exon VII 600 | Exon VII 638 | Exon VII 645 | Exon VII 667 | I7-16 | I7-69 | I7-120 | Exon VIII 902 | Exon VIII 973 | Allele Frequency 61 Hepatic Biopsy Samples | Allele Frequency 150 Random Blood Donors |
|---|---|---|---|---|---|---|---|---|---|---|---|---|
| *1A | G | G | G | G | A | C | T | C | A | C | 0.328 | 0.303 |
| *1B | G | G | G | G | A | C | T | C | A | C | 0.221 | 0.237 |
| *1C | A | C | G | A | A | C | C | C | A | T | 0.041 | 0.040 |
| *1D | G | G | G | G | A | C | T | C | A | C | 0.016 | 0.027 |
| *1E | G | G | G | G | A | C | T | G | A | C | 0.016 | 0.020 |
| *1F | G | G | G | G | A | C | T | C | A | C | 0.033 | 0.017 |
| *1G | G | G | G | G | A | C | T | C | A | C | N.D. | 0.010 |
| *1H | G | G | G | G | A | C | C | C | A | C | N.D. | 0.010 |
| *1I | G | G | G | G | A | C | T | C | A | C | N.D. | 0.007 |
| *1J | A | C | G | G | A | C | C | C | G | T | 0.008 | N.D. |
| *1K | A | C | G | A | A | C | C | C | A | C | 0.008 | N.D. |
| *2 | A | C | A | G | A | T | C | C | G | T | 0.311 | 0.313 |
| *3A | G | G | G | G | G | C | T | C | A | C | N.D. | 0.007 |
| *3B | G | G | G | G | G | C | T | C | A | C | 0.016 | 0.003 |
| *4 | G | G | G | G | A | C | T | C | A | C | N.D. | 0.003 |

TABLE 4

SULT1A1 ALLOZYMES

| Allozyme | Amino Acid 37 | Amino Acid 213 | Amino Acid 223 | Allozyme Frequency 61 Hepatic Biopsy Samples | Allozyme Frequency 150 Random Blood Donors |
|---|---|---|---|---|---|
| *1 | Arg | Arg | Met | 0.671 | 0.674 |
| *2 | Arg | His | Met | 0.311 | 0.313 |
| *3 | Arg | Arg | Val | 0.016 | 0.010 |
| *4 | Gln | Arg | Met | N.D. | 0.003 |

The newly discovered alleles for SULT1A2 appeared to be in linkage disequilibrium with alleles for SULT1A1. SULT1A1*1 and *3 were linked to SULT1A2*1 and *3 while SULT1A1*2 was linked to SULT1A2*2. In this analysis, the hypothesis of no association between the two polymorphisms was rejected, but the hypothesis of association was supported with $x^2=53.83$ (p<0.0001). Of the 122 sets of 1A1/1A2 alleles sequenced for each gene, only ten displayed discordance. The linkage disequilibrium complicated attempts to determine which of these two gene products might be responsible for phenol SULT phenotype. Therefore, to clarify possible genotype-phenotype correlations for these enzymes, biochemical and physical properties of the proteins encoded by all common alleles for SULT1A1 and SULT1A2 were determined.

2.2 COS-1 Cell Expression of SULT1A1 and SULT1A2 Allozymes

Expression constructs for each of the common (frequencies≧1%) allozymes for SULT1A1 and SULT1A2 were used to transfect COS-1 cells. Selected biochemical and physical properties of the expressed enzymes were then determined. Those properties included apparent $K_m$ values for the two cosubstrates for the enzyme reaction (4-nitrophenol and PAPS); thermal stability; and sensitivity to inhibition by DCNP. The substrate kinetic experiments were performed in two steps. Initially a wide range of concentrations of 4-nitrophenol that varied over at least three orders of magnitude was tested, followed by detailed study of concentrations close to the apparent $K_m$ value for that allozyme. Concentrations of 4-nitrophenol that were used to calculate apparent $K_m$ values ranged from 0.02 to 5.0 $\mu$M for SULT1A1*1, 1A1*2 and 1A1*3; 0.08 to 10.0 $\mu$M for SULT1A2*1 and 1A2*3; 1.0 to 1000 $\mu$M for SULT1A2*2; and 3.9 to 3000 $\mu$M for SULT1A3. Data from these experiments were then used to construct double inverse plots that were used to calculate apparent $K_m$ values (Table 5). The results of the substrate kinetic studies suggested that TS PST phenotype in human liver might be due primarily to the expression of SULT1A1, since optimal conditions for the assay of TS PST activity in the human liver involved the use of 4 μM 4-nitrophenol as a substrate. See, Campbell, N. R. C. et al., *Biochem. Pharmacol.*, 36:1435–1446 (1987). This concentration would be optimal for assay of the activities of allozymes encoded by alleles for SULT1A1, but was below the apparent $K_m$ values for all of the SULT1A2 allozymes. Of particular importance for the genotype-phenotype correlation analysis described subsequently is the fact that SULT1A2*2 has a very high apparent $K_m$ value for 4-nitrophenol (Table 5).

Apparent $K_m$ values of the recombinant SULTs for PAPS were also determined. In those studies, as well as in the thermal stability and DCNP inhibition experiments, the concentrations of 4-nitrophenol used to perform the assays were 4 μM for SULT1A1*1, *2, and *3; 100 μM for SULT1A2*1; 50 μM for 1A2*3; and 3000 μM for SULT1A2*2 and SULT1A3. These concentrations were based on results of the 4-nitrophenol substrate kinetic experiments and represented the concentration at which maximal activity had been observed for that particular allozyme. Apparent $K_m$ values of the recombinant SULT proteins for PAPS are also listed in Table 5. With one exception, those values varied from approximately 0.2 to 1.2 μM. The single exception was SULT1A2*1, with an apparent $K_m$ value approximately an order of magnitude lower than those of the other enzymes studied (Table 5). Each value in Table 5 represents the mean ±SEM of nine separate determinations.

The thermal stabilities of the seven expressed proteins were also determined and varied widely. The rank order of the thermal stabilities was 1A2*2>1A2*1>>1A1*1≅1A1*3≅1A2*3>1A1*2>>1A3 (Table 5). These observations were consistent with experiments described herein that indicated that SULT1A1*2 was associated with a "thermolabile" phenotype in the platelet (FIG. 1) since that allele had the lowest $T_{50}$ value of the recombinant "TS-PST-like" allozymes studied (Table 5). It is unlikely that allozyme SULT1A2*2 could explain a "thermolabile" phenotype since it was the most "thermostable" of the allozymes studied.

Finally, sensitivity of the recombinant proteins to inhibition by DCNP was determined. Sixteen different concentrations of DCNP, ranging from 0.01 to 1000 μM, were tested with each recombinant allozyme. $IC_{50}$ values for DCNP also varied widely, with SULT1A2*3 being most, and SULT1A3 least sensitive to inhibition (Table 5). After all of these data had been obtained, the final step in this series of experiments was an attempt to correlate human liver TS PST phenotype with SULT1A1 and/or SULT1A2 genotype.

TABLE 5

RECOMBINANT HUMAN SULT BIOCHEMICAL AND PHYSICAL PROPERTIES

| Allozyme | Apparent Km (μM) | | Thermal Stability | DCNP Inhibition |
|---|---|---|---|---|
| | 4-Nitrophenol | PAPS | $T_{50}$ (° C.) | $IC_{50}$ (μM) |
| SULT1A1 | | | | |
| *1 | 0.88 ± 0.07 | 1.21 ± 0.02 | 39.3 ± 0.64 | 1.44 ± 0.11 |
| *2 | 0.78 ± 0.08 | 0.98 ± 0.03 | 37.2 ± 0.43 | 1.38 ± 0.28 |
| *3 | 0.31 ± 0.01 | 0.17 ± 0.02 | 38.9 ± 0.03 | 1.32 ± 0.27 |
| SULT1A2 | | | | |
| *1 | 8.70 ± 1.10 | 0.05 ± 0.001 | 43.6 ± 0.15 | 6.94 ± 0.55 |
| *2 | 373 ± 33 | 0.50 ± 0.001 | 46.3 ± 0.09 | 44.4 ± 1.50 |
| *3 | 5.65 ± 1.14 | 0.28 ± 0.006 | 38.8 ± 9.19 | 0.97 ± 0.001 |
| SULT1A3 | 4960 ± 810 | 0.28 ± 0.001 | 32.6 ± 0.19 | 86.9 ± 6.00 |

2.3 Human Liver Genotype-Phenotype Correlation

Figure 1B:
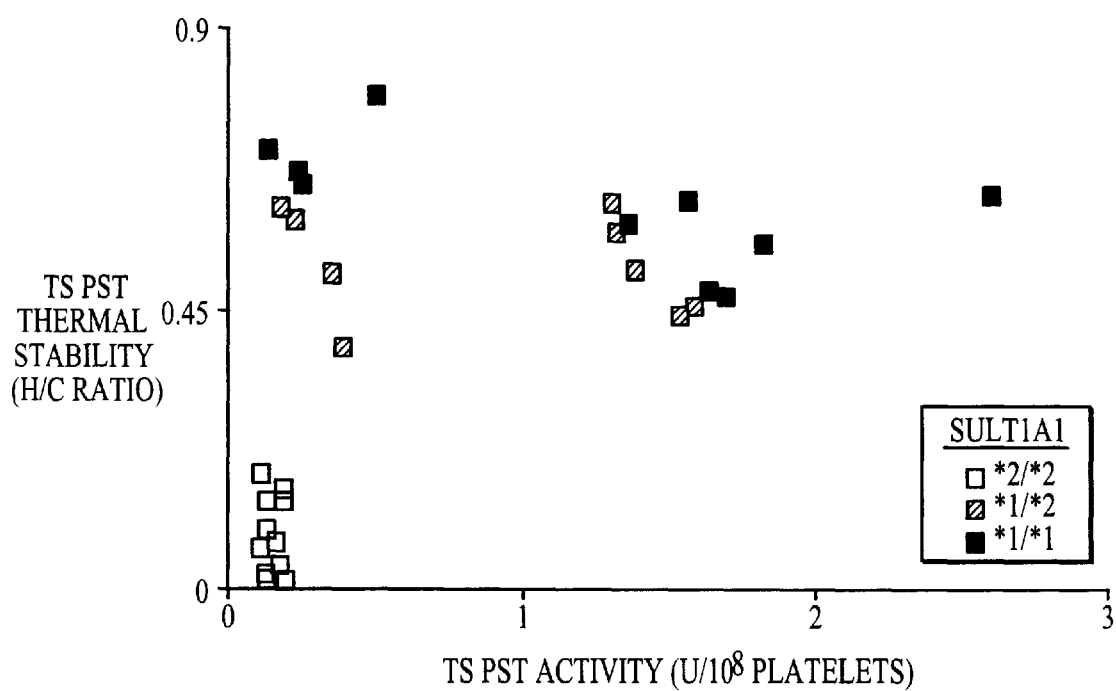
Figure 4A:
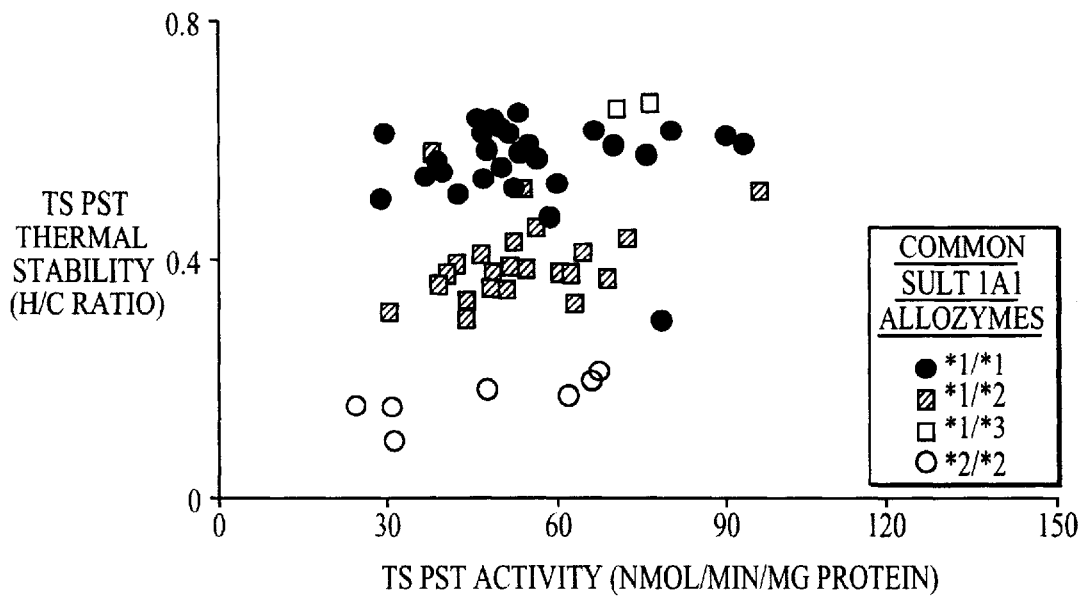
FIGS. 4A and 4B are scattergrams that depict the correlation of SULT1A1 and SULT1A2 genotypes with human liver TS PST phenotype. TS PST phenotypes in the human liver samples depicted as in FIG. 3 are shown with (A) common SULT1A1 allozymes or (B) common SULT1A2 allozymes superimposed. In (B) three samples are not shown because they contain SULT1A2 allozymes that were observed only once in this population sample.
Figure 4B:
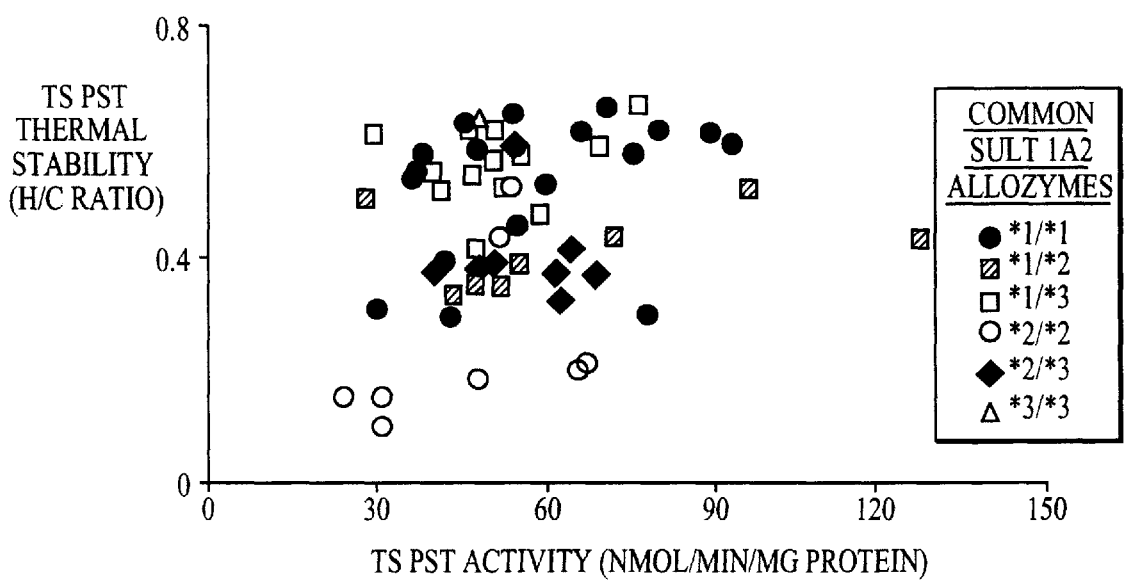

TS PST activity and thermal stability was measured in human platelet samples (n=905) and human liver biopsy samples (n=61). A scattergram of these data are shown in FIG. 1 and 2. Subjects homozygous for the allele SULT1A1*2 uniformly had low levels of both TS PST activity and thermal stability in their platelets (FIG. 1B). The genotype-phenotype correlation for SULT1A1 in the liver samples is shown in FIG. 4A. Similar data for SULT1A2 are plotted in FIG. 4B. FIG. 4 demonstrates that the SULT1A1*2 allele appeared to be associated with low TS PST thermal stability in the liver, just as it was in the human blood platelet (FIG. 1B). For example, the average H/C ratio for samples homozygous for SULT1A1*1 was 0.57±0.01 (n=28, mean±SEM), while that for heterozygous 1A1*1/1A1*2 samples was 0.40±0.01 (n=24) and that for samples homozygous for SULT1A1*2 was 0.18±0.01 (n=7, p<0.001 by ANOVA). Table 6 summarizes this data.

TABLE 6

SULT1A1 ALLOZYMES AND TS PST ACTIVITY

| Platelet Allozyme | AA 213 | N | H/C Ratio | N | TS PST activity |
|---|---|---|---|---|---|
| *1/*1 | Arg/Arg | 11 | 0.62 ± 0.03** | 11 | 1.08 ± 0.25 |
| *1/*2 | Arg/His | 8 | 0.53 ± 0.03** | 9 | 0.90 ± 0.20 |
| *2/*2 | His/His | 13 | 0.09 ± 0.02** | 13 | 0.14 ± 0.01 |
| Liver | | | | | |
| *1/*1 | Arg/Arg | 28[a] | 57.5 ± 1.31* | 28[a] | 56.0 ± 3.05 |
| *1/*2 | Arg/His | 24 | 40.5 ± 1.38* | 24 | 56.8 ± 4.19 |
| *2/*2 | His/His | 7 | 17.7 ± 1.44* | 3[b] | 28.5 ± 2.27** |

*p < 0.0001 by ANOVA compared with other two groups;
**p < 0.02 by ANOVA compared with other two groups;
[a]Two samples heterozygous for SULT1A*3 were not included in these analyses;
[b]Four malignant hepatic samples homozygous for SULT1A1*2 were not included in this analysis.

Although the SULT1A1*2 allele was highly correlated with low TS PST thermal stability in the liver, unlike the situation in the platelet, low thermal stability was not significantly correlated with low levels of TS PST activity (FIG. 4A). Of possible importance is the fact that, when the data were stratified on the basis of diagnosis, of the seven samples homozygous for SULT1A1*2, the three from patients with benign hepatic disease had the lowest levels of TS PST activity, while the four samples from patients with malignant disease had the highest activity (28.5±2.3 vs. 59.8±4.0, mean±SEM respectively, p<0.002).

The results of the substrate kinetic experiments (Table 5), as well as the results of the thermal stability studies suggested that TS PST phenotype in the liver was most likely a measure of SULT1A1 expression. As pointed out previously, that was true because both $K_m$ values for 4-nitrophenol and $T_{50}$ values for recombinant SULT1A2 allozymes were above those found to be optimal for the determination of TS PST phenotype in human liver cytosol preparations (Table 5). Testing that hypothesis directly is complicated by the fact that SULT1A1 and 1A2 share 95% or greater identity for both protein amino acid and mRNA nucleotide sequences; so neither Western nor Northern blots can easily distinguish between them. However, biochemical studies of recombinant SULT allozymes suggested that the sulfation of 100 μM 4-nitrophenol might represent a relatively specific measure of SULT1A2 activity (Table 5). As a result of the profound substrate inhibition which these enzymes display, SULT1A1 allozymes show little or no activity at that concentration, and SULT1A3 would not contribute significantly to activity measure at that concentration because of its very high $K_m$ value for 4-nitrophenol (Table 6). Therefore, 100 μM 4-nitrophenol was used as a substrate with cytosol from six pooled liver samples in an attempt to measure SULT1A2 activity. However, after three attempts no activity was detected, suggesting that SULT1A2 is not highly expressed in the liver. Ozawa, S. et al., *Chem. Biol. Interact.*, 109:237–248 (1998).

In summary, common genetic polymorphisms were observed for both SULT1A1 and SULT1A2 in humans. However, the proteins encoded by these alleles differed in their biochemical and physical properties. Recombinant SULT1A2*2 had a $K_m$ value dramatically higher than did SULT1A2*1 or 1A2*3. The allele SULT1A1*2 was associated with decreased TS PST thermal stability in the liver and in the blood platelet. Unlike the situation in the platelet, SULT1A1 or SULT1A2 alleles identified in the hepatic tissues did not appear to be systematically associated with level of TS PST activity.

2.4 SULT1A3 Polymorphisms

All exons and introns for SULT1A3 were sequenced using DNA from 150 random blood donor samples to detect nucleotide polymorphisms. Table 7 describes sequence variants.

TABLE 7

| | Nucleotide Transition/Transversion and Position Within SULT1A3 Gene | | | | |
|---|---|---|---|---|---|
| Classification | Exon 3 105 | I3-83/84 Insertion | I4-69 | I6-69 | I7-113 |
| Wild Type | A | — | G | G | G |
| Variant | G | CAGT | A | A | T |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a SULT1A1 nucleic acid sequence, wherein said SULT1A1 nucleic acid sequence comprises a nucleotide sequence variant and nucleotides flanking said sequence variant, and wherein said nucleotide sequence variant is selected from the group consisting of a cytosine at nucleotide 138 of intron 1A, a thymine at nucleotide 34 of intron 5, an adenine at nucleotide 57 of the coding sequence, an adenine at nucleotide 110 of the coding sequence, and an adenine at nucleotide 645 of the coding sequence.

2. The isolated nucleic acid molecule of claim 1, wherein said SULT1A1 nucleic acid sequence encodes a sulfotransferase polypeptide having a glutamine at amino acid residue 37.

3. An isolated nucleic acid molecule comprising a sulfotransferase nucleic acid sequence, wherein said sequence encodes a sulfotransferase allozyme selected from the group consisting of SULT1A1*4, SULT1A2*4, SULT1A2*5, and SULT1A2*6.

* * * * *

SEQUENCE LISTING

<160> NUMBER OF SEQ ID NOS: 52

<210> SEQ ID NO 1
<211> LENGTH: 23
<212> TYPE: DNA
<213> ORGANISM: Artificial Sequence
<220> FEATURE:
<223> OTHER INFORMATION: primer

<400> SEQUENCE: 1
ccacggtctc ctctggcagg ggg                                            23

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
gttgaggagt tggctctgca gggtc                                          25

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
cacgtactcc agtggcgggc cctag                                          25

<210> SEQ ID NO 4
<211> LENGTH: 18

```
<212> TYPE: DNA
<213> ORGANISM: Artificial Sequence
<220> FEATURE:
<223> OTHER INFORMATION: primer

<400> SEQUENCE: 4
ggaaccacca cattagaa                                                   18

<210> SEQ ID NO 5
<211> LENGTH: 26
<212> TYPE: DNA
<213> ORGANISM: Artificial Sequence
<220> FEATURE:
<223> OTHER INFORMATION: primer

<400> SEQUENCE: 5
cctggagacc ttcacacacc ctgata                                          26

<210> SEQ ID NO 6
<211> LENGTH: 25
<212> TYPE: DNA
<213> ORGANISM: Artificial Sequence
<220> FEATURE:
<223> OTHER INFORMATION: primer

<400> SEQUENCE: 6
ccactctgcc tggcccacaa tcata                                           25

<210> SEQ ID NO 7
<211> LENGTH: 23
<212> TYPE: DNA
<213> ORGANISM: Artificial Sequence
<220> FEATURE:
<223> OTHER INFORMATION: primer

<400> SEQUENCE: 7
gctggggaac caccgcatta gag                                             23

<210> SEQ ID NO 8
<211> LENGTH: 23
<212> TYPE: DNA
<213> ORGANISM: Artificial Sequence
<220> FEATURE:
<223> OTHER INFORMATION: primer

<400> SEQUENCE: 8
aactcccaac ctcacgtgat ctg                                             23

<210> SEQ ID NO 9
<211> LENGTH: 23
<212> TYPE: DNA
<213> ORGANISM: Artificial Sequence
<220> FEATURE:
<223> OTHER INFORMATION: primer

<400> SEQUENCE: 9
cctcaggttc ctcctttgcc aat                                             23

<210> SEQ ID NO 10
<211> LENGTH: 23
<212> TYPE: DNA
<213> ORGANISM: Artificial Sequence
<220> FEATURE:
<223> OTHER INFORMATION: primer

<400> SEQUENCE: 10
```

-continued

```
tgccaaggga gggggctggg tga                                                23

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
gttgaggagt tggctctgca gggtc                                              25

<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
ccactctgcc tggcccacaa tcata                                              25

<210> SEQ ID NO 13
<211> LENGTH: 28
<212> TYPE: DNA
<213> ORGANISM: Artificial Sequence
<220> FEATURE:
<223> OTHER INFORMATION: primer

<400> SEQUENCE: 13
gggccccgtt ccacgagggt gctttcac                                           28

<210> SEQ ID NO 14
<211> LENGTH: 34
<212> TYPE: DNA
<213> ORGANISM: Artificial Sequence
<220> FEATURE:
<223> OTHER INFORMATION: primer

<400> SEQUENCE: 14
tgaccccact aggaagggag tcagcacccc tact                                    34

<210> SEQ ID NO 15
<211> LENGTH: 19
<212> TYPE: DNA
<213> ORGANISM: Artificial Sequence
<220> FEATURE:
<223> OTHER INFORMATION: primer

<400> SEQUENCE: 15
ggaaccacca cattagaac                                                     19

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
tggaacttct ggcttcaagg gatct                                              25

<210> SEQ ID NO 17
<211> LENGTH: 23
<212> TYPE: DNA
<213> ORGANISM: Artificial Sequence
```

```
<220> FEATURE:
<223> OTHER INFORMATION: primer

<400> SEQUENCE: 17
cctcagcttc ctcctttgcc aaa                                              23

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
tggctgggtg gccttggc                                                    18

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
gctggctcta tgggttttga agt                                              23

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
ctggagcggg gaggtggccg tatt                                             24

<210> SEQ ID NO 21
<211> LENGTH: 30
<212> TYPE: DNA
<213> ORGANISM: Artificial Sequence
<220> FEATURE:
<223> OTHER INFORMATION: primer

<400> SEQUENCE: 21
aatgcccgca acagtgcctg ctgcatagag                                       30

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
acgctgcccg gcggactcga cgtcctccac catctt                                36

<210> SEQ ID NO 23
<211> LENGTH: 23
<212> TYPE: DNA
<213> ORGANISM: Artificial Sequence
<220> FEATURE:
<223> OTHER INFORMATION: primer

<400> SEQUENCE: 23
gagaatccca ctttcttgct gtt                                              23
```

```
<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gggaacagtc tatgccacca tac                                              23

<210> SEQ ID NO 25
<211> LENGTH: 23
<212> TYPE: DNA
<213> ORGANISM: Artificial Sequence
<220> FEATURE:
<223> OTHER INFORMATION: primer

<400> SEQUENCE: 25
ggttcctcct ttgccagttc aac                                              23

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
ggactaagta tctgatccgt gg                                               22

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
gggccccagg ggttgaggct ctt                                              23

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
atatgtggcc ccaccgggca ttc                                              23

<210> SEQ ID NO 29
<211> LENGTH: 7152
<212> TYPE: DNA
<213> ORGANISM: Homo sapiens
<220> FEATURE:
<221> NAME/KEY: CDS
<222> LOCATION: (3810)...(3956)
<221> NAME/KEY: CDS
<222> LOCATION: (4061)...(4186)
<221> NAME/KEY: CDS
<222> LOCATION: (4276)...(4374)
<221> NAME/KEY: CDS
<222> LOCATION: (5584)...(5709)
<221> NAME/KEY: CDS
<222> LOCATION: (5805)...(5900)
<221> NAME/KEY: CDS
<222> LOCATION: (6426)...(6605)
<221> NAME/KEY: CDS
```

<222> LOCATION: (6728)...(6837)

<400> SEQUENCE: 29

```
ttgctgccag ctgcctctcc ctccttgtct cttacctgcc tgctgcctgg gacaggatga      60
agcgggccc ttgtgttgcc ccaaccctgg ctgttggcta agagcccacg tgatctgcct     120
gtgagaggag ttccttccgg aagaaccagg gcagcttctg cccctagagg gccaatgccc     180
tagctgagtg cagtcccccg gccccagcct ggtccagctt tgggaagagg gtgcccagtt     240
gtgcaatcca ggccggggca gccgtgtcct gatcttggta ttcagggctg agcctggagg     300
gggcttgtga tgcctgactc tgtctccctc tctggcccca tgccttggta gctgtgaggc     360
gtcactgctt tgggtgacct gatctggctg tgatggatga gcacggggga aatagtggaa     420
gactcggaat tagaagacgt gagtgggctt tggccccagc ctccctaccc cactccctgt     480
cctgggctgc ctgtgaccaa cctcgtttct gcaggcacac tggatagccc tgctggagct     540
cagtgtccct aatcccctcc agatactggt ggcctagggg aggtcatcaa aaaccggtgg     600
gacatcgacc tcagcccgtt tccacgcttt ttttgtttt tttttttttt ttgagaccga     660
gtttcactct tgttgcccag gctggagtgc aatggcgtga tcttggctca ccgcaacctc     720
cgcctcctgg gttcaagcga ttctcctgcc tcagcctccc aagtagctgg gattccaggc     780
gtgtgccacc aggcttgact aatttttctat ttttagtaga caaggtttt ctccatgttg     840
gtcaggctgg tctcaaactc ccgacttcag gtgatctgcc tgcctcggcc ccccaaagtg     900
ctgggattac aggagtgagc caccgtgcca ggccttctcc aggctcttgg caccttagcc     960
agaaacaatt taaggacaag tgcaaaagtc atgaatgtag gcagatttcc tgcagagtaa    1020
agggactcac tcaagaagag gaacgtgggg gtcctcaaga gagtgtctca tgccctacaa    1080
ggtgtgggc tgacctttat gggcttcttc aactaaagag gggtatattc atgaagagtc    1140
caggaaaagg taaagatttc tcaagaccgt ggtgccacaa tttacaccca aatacaggtg    1200
ttcctggagc cgtcttggca ctggtgggtg tacggtttca tatgttactg atcatacaat    1260
gagatcctag gtgaaaccta catcaaatac agcgccatgt tgtgtctggt tggtcgtggc    1320
cagcttggtc ctcatcctat ttttcaggga cttattggcc cttagcgcat gcagctattt    1380
caagtttcct tcttctcctc atgtgaaact gctgcctggg atttttgtatt cacttgctac    1440
cactctatta atctcacatt ctcgcctctt ttctgtgtca ccccgtgtgg gtccgacagg    1500
ttgttactag agtgcaatac aaagtcttag tcaagggaac ctcctgaggg ttgctgaggg    1560
cagggtgga gctagtagcc tgaggacctg ccagtcacgg ggattcctca tgggcacaga    1620
ggagggagga ggggtccatg gccctagcat atgagaagcc tctcctctgc ctggaattcc    1680
catgcctcag cttcccccac actcccacct gtccgcttgc ctctgaactc acgcatttct    1740
tggaagtctt gggagattca cctttactca gatggttgtt tacctgtctc gtgcacagct    1800
tgaccttgga ctttaaagtg aggataaaga acgaggagga tggggggatg ccccccttcc    1860
acgggccctg tggcttccaa acctcggcct cctctggtct cttgtctgtg gagcctcctt    1920
caaacccagg gaaataaaac cacctgccac gggttgtggt tcttctagga tcttctatca    1980
atgttctctg aggtccccag gagccatgaa gctgggctg actcccaggg caatgggact    2040
gcagtgtcct tgttctttct tgttctatgc atccatgctc tgctccaccc ctgccccttc    2100
actctgccca cacacatccc tctagactgg ccttgtggtc agagcctgga gtgcatgggc    2160
tgctgggggc ctgtgggctg cactgggcca gaacccctgg caccttcaag actggcctgg    2220
agccagcagg taggtgacct ttccagggcc tgcctatccc agctttctcc tccaatccct    2280
```

-continued

```
cccctctctt gcctgggtca attagagaga gcttgtctgt tggctgcctg gcggggtgga      2340
gttcaggggc aggtcaggag cccagtgaca gctcggaaaa aaaaaaaaaa aaaaaaaaa      2400 cagaaaaaaa aacctacaaa aacaaaccca ccattgggcc tttccccttt cattcttctg      2460
ttttctacac agcaaactca gtcgtggctt tggagatcac tttaagcttg tctccagctg      2520
gcacactaag gagggtaatg gagaagctcc cccaccccca accccacccc ttccttccgg      2580
aagcaaatct aagtccagcc ccggctccag atccctccca cagtggacct aggaaaccct      2640
cagctcagag aacaaccctg cattccccac acagcaccca caatcagcca ctgcgggcga      2700
ggagggcacg aggccaggtt cccaagagct caggtgagtg acacagtgga acggcccagg      2760
gcgccctcac cctgctcagc ttgtggctct aacattccag aagctgaggc ctctggcatc      2820
cctgcccttt ccccatggat atcccatttc agacaaccct ggcctgcgtg aatccccctc      2880
ccttcccttg tttgtttgtt tttttccccg ggggaggcca ggtcttgctg tcacccaggc      2940
tggagtgctg tgggatcctg gccactgcag ccttgaattc ctgggctcaa gtgattctct      3000
tgccacagcc tctggagtag ctaggactac aggccctcat catcctgcct ggttaatgtt      3060
taagaatttt tttaaagatt tttagagatg gggtcttgca atgctgcacc aggttggtct      3120
ccaactcctg gcctcagcct ccctagggtc tgggattata ggtgggagcc accctgccta      3180
ggcctgtgct tttgctgagt catcagagtt ttgttcattc ccacagcagc tctggcccct      3240
agtagcagct cagttcctca atgggccgtg tttgtcctgg agcccagatg gactgtggcc      3300
aggcaagtgg atcacaggcc tggctggcct gggcggtttc cacatgtgag gggctgaggg      3360
gctcaaggag gggagcatct ccactgggtg gaggctgggg gtcccagcag gaaatggtga      3420
gacaaagggc gctggctggc agggagacag cacaggaagg tcctagagct tcctcagtgc      3480
agctggactc tcctggagac cttcacacac cctgatatct gggccttgcc cgacgagggt      3540
gctttcactg gtctgcacca tggcccaggc cctgggattt tgaacagctc cgcaggtgaa      3600
tgaaaggtga ggccaggctg gggaaccacc gcattagagc ccgacctggt tttcagcccc      3660
agccccgcca ctgactggct tgtgagtgc gggcaagtca ctcagcctcc ctaggcctca      3720
gtgacttccc tgaaagcaag aattccactt tcttgctgtt gtgatggtgg taagggaacg      3780
ggcctggctc tggcccctga cgcaggaac atg gag ctg atc cag gac acc tcc      3833
                                   Met Glu Leu Ile Gln Asp Thr Ser
                                    1               5 cgc ccg cca ctg gag tac gtg aag ggg gtc ccg ctc atc aag tac ttt      3881
Arg Pro Pro Leu Glu Tyr Val Lys Gly Val Pro Leu Ile Lys Tyr Phe
    10                  15                  20 gca gag gca ctg ggg ccc ctg cag agc ttc cag gcc cgg cct gat gac      3929
Ala Glu Ala Leu Gly Pro Leu Gln Ser Phe Gln Ala Arg Pro Asp Asp
 25                  30                  35                  40 ctg ctc atc agc acc tac ccc aag tcc ggtaagtgag gagggccacc            3976
Leu Leu Ile Ser Thr Tyr Pro Lys Ser
                 45 caccctctcc caggtggcag tccccacctt ggccagcgag gtcgtgccct cagcctgctc      4036 accccccatc tccctccctc tcca ggc acc acc tgg gtg agc cag att ctg       4087
                            Gly Thr Thr Trp Val Ser Gln Ile Leu
                             50                  55 gac atg atc tac cag ggt ggt gac ctg gag aag tgt cac cga gct ccc      4135
Asp Met Ile Tyr Gln Gly Gly Asp Leu Glu Lys Cys His Arg Ala Pro
 60                  65                  70 atc ttc atg cgg gtg ccc ttc ctt gag ttc aaa gcc cca ggg att ccc      4183
Ile Phe Met Arg Val Pro Phe Leu Glu Phe Lys Ala Pro Gly Ile Pro
```

-continued

```
          75                  80                  85                  90
tca ggtgtgtgag tgtgtcctgg gtgcaagggg agtggaggaa gacagggctg              4236
Ser gggcttcagc tcaccagacc ttccctgacc cactgctca ggg atg gag act ctg          4290
                                            Gly Met Glu Thr Leu
                                                             95 aaa gac aca ccg gcc cca cga ctc ctg aag aca cac ctg ccc ctg gct         4338
Lys Asp Thr Pro Ala Pro Arg Leu Leu Lys Thr His Leu Pro Leu Ala
            100                 105                 110 ctg ctc ccc cag act ctg ttg gat cag aag gtc aag gtgaggcagg              4384
Leu Leu Pro Gln Thr Leu Leu Asp Gln Lys Val Lys
        115                 120 gcacagtgtt tcacatccat aatcccagca ctttgggagg ctgaggcagg cagatcacct       4444
gaggttggga gtttgagagc accctgagca acatagaaga accttgtctc tactaaaaat       4504
acagaattag ccgggtgtgg tggcgggtgc ctgtaatccc agctactccg aagcctgaga       4564
caggagaatc acttgaaccc gggagaagga ggttgtggtg agccagagat cccaccattg       4624
cattccagcc tgagcaacaa gagcaaaact cacaaaaata aataaataaa tagatatata       4684
aataaaaata aaactgtggc acctgtggtg gctcactgct gtaatgccag cactttggga       4744
ggccaaattg ggtggatcac ttgagctcag gagttacaga ccagcccggg aaacatgggg       4804
aacttccatc tctataaaaa tgcaaaatat cagcagggca tggtggcatg cgctgtagt        4864
tccagctact ggaaagtctg aggttggagg attgcttgag cctgggaggt caaggttgca       4924
gtgagttatt atcactccag tgcactccaa cctgggcgac agaaaaaaag aaagaccaag       4984
gtctttttc tttttgaga ttgtctcaat aaataaataa atgaataaat aaaaataaaa         5044
taaagtaaaa taaatcccac aattaaaga aaaagcaaag gtccaggtgt ggggcatgtg        5104
aatccaggga aggaggccct ggctcagccc agctttggtc ctgttcttct gggaaagtcg       5164
cctcacttcc tccagccttg tctcatcttc tgcggcgggg actgtctgcc tcttgctctg       5224
atgaccaaga acgtaaggct cttcagtgta gacctaagaa agctagaggg tgggtcctca       5284
caggcccaca aaatttggtg gcggtgggat cacggctggt ggagcgtgcc ttgctccaga       5344
tcggggtgtg acgcattgat gcagattata ttgctataga atatgatggt ctcagggacc       5404
aggcaggact ttggcttctg agcagggttc agatcctgac ttggccctac cggtgccgtg       5464
agatctcaaa caagtcagcc tctaagcctc aggttcctcc tttgccaatc aagagatga       5524
gctggcctgg ggcaggctgt gtggtgatgg tgctggggtt gagtcttctg cccctgcag        5583 gtg gtc tat gtt gcc cgc aac gca aag gat gtg gca gtt tcc tac tac        5631
Val Val Tyr Val Ala Arg Asn Ala Lys Asp Val Ala Val Ser Tyr Tyr
125                 130                 135                 140 cac ttc tac cac atg gcc aag gtg cac cct gag cct ggg acc tgg gac        5679
His Phe Tyr His Met Ala Lys Val His Pro Glu Pro Gly Thr Trp Asp
                145                 150                 155 agc ttc ctg gag aag ttc atg gtc gga gaa ggtgggtttg atgggaggaa          5729
Ser Phe Leu Glu Lys Phe Met Val Gly Glu
            160                 165 ggaaagtgtg gagccgaggg gtggtggcta caacgcacag caaccctgtg ttggcacccc      5789
ttgcctgctt ctcca gtg tcc tac gga tcc tgg tac cag cac gtg cag gag       5840
                Val Ser Tyr Gly Ser Trp Tyr Gln His Val Gln Glu
                                170                 175 tgg tgg gag ctg agc cgc acc cac cct gtt ctc tac ctc ttc tat gaa        5888
Trp Trp Glu Leu Ser Arg Thr His Pro Val Leu Tyr Leu Phe Tyr Glu
180                 185                 190
```

```
gac atg aag gag gtgagaccac ctgtgaagct tccctccatg tgacacctgg          5940
Asp Met Lys Glu
195 gggccggcac ctcacaggga cccaccaggg tcacccagcc cctcccttg gcagccccca    6000 cagcaggccc ggattcccca tcctgccttc ttggcccagg cctccccgct acaggcccca    6060 cctggcagcg ggccccacac ggctctcatc acccacatct gagtcagctg catgggggc    6120 cacggatcag aaacttagtc ctattgctac tccctgccaa agggtgtgcc acccagggcc    6180 acagtcatgg aagaagacca tcacggtcct cacccatagg agccaagccc agctcatgat    6240 gggatcacag gcagacagc aattcttttt accccgggga ctggggccct gggggttgag      6300 gagttggctc tgcagggtct ctaggagagg tggccagatc gcctctgagg ttagagaagg    6360 ggaccccttt tacttttcct gaatcagcaa tccgagcctc cactgaggag ccctctgctg    6420 ctcag aac ccc aaa agg gag att caa aag atc ctg gag ttt gtg ggg cac   6470
      Asn Pro Lys Arg Glu Ile Gln Lys Ile Leu Glu Phe Val Gly His
          200             205                 210 tcc ctg cca gag gag acc gtg gac ttc atg gtt cag cac acg tcg ttc      6518
Ser Leu Pro Glu Glu Thr Val Asp Phe Met Val Gln His Thr Ser Phe
   215                 220                 225 aag gag atg aag aag aac cct atg acc aac tac acc acc gtc ccc cag     6566
Lys Glu Met Lys Lys Asn Pro Met Thr Asn Tyr Thr Thr Val Pro Gln
230                 235                 240                 245 gag ttc atg gac cac agc atc tcc ccc ttc atg agg aaa gtgggtgct       6615
Glu Phe Met Asp His Ser Ile Ser Pro Phe Met Arg Lys
                250                 255 ggccagtacg ggggtttggg gcgggtggga gcagcagctg cagcctcccc ataggcactc    6675
ggggcctccc ctgggatgag actccagcct tgctccctgc cttcccccc ca ggc atg   6733
                                                            Gly Met
                                                                260 gct ggg gac tgg aag acc acc ttc acc gtg gcg cag aat gag cgc ttc    6781
Ala Gly Asp Trp Lys Thr Thr Phe Thr Val Ala Gln Asn Glu Arg Phe
            265                 270                 275 gat gcg gac tat gcg gag aag atg gca ggc tgc agc ctc agc ttc cgc    6829
Asp Ala Asp Tyr Ala Glu Lys Met Ala Gly Cys Ser Leu Ser Phe Arg
        280                 285                 290 tct gag ct gtgagagggg ctcctgggt cactgcagag ggagtgtgcg aatcaaacct   6887
Ser Glu gaccaagcgg ctcaagaata aaatatgaat tgagggcctg ggacggtagg tcatgtctgt    6947
aatcccagca atttggaggc tgaggtggga ggatcatttg agcccaggag ttcgagacca    7007
acctgggcaa catagtgaga ttctgttaaa aaataaaat aaaataaaac caattttaa     7067 aaagagaata aatatgatt gtgggccagg catagtggct catgcctgta atcccagcaa    7127
tttgagaagt tgaggctaga ggatc                                         7152

<210> SEQ ID NO 30
<211> LENGTH: 49
<212> TYPE: PRT
<213> ORGANISM: Homo sapiens

<400> SEQUENCE: 30

Met Glu Leu Ile Gln Asp Thr Ser Arg Pro Pro Leu Glu Tyr Val Lys
1               5                   10                  15

Gly Val Pro Leu Ile Lys Tyr Phe Ala Glu Ala Leu Gly Pro Leu Gln
            20                  25                  30

Ser Phe Gln Ala Arg Pro Asp Asp Leu Leu Ile Ser Thr Tyr Pro Lys
        35                  40                  45
```

Ser

<210> SEQ ID NO 31
<211> LENGTH: 42
<212> TYPE: PRT
<213> ORGANISM: Homo sapiens

<400> SEQUENCE: 31

Gly Thr Thr Trp Val Ser Gln Ile Leu Asp Met Ile Tyr Gln Gly Gly
 1               5                  10                  15

Asp Leu Glu Lys Cys His Arg Ala Pro Ile Phe Met Arg Val Pro Phe
            20                  25                  30

Leu Glu Phe Lys Ala Pro Gly Ile Pro Ser
        35                  40

<210> SEQ ID NO 32
<211> LENGTH: 33
<212> TYPE: PRT
<213> ORGANISM: Homo sapiens

<400> SEQUENCE: 32

Gly Met Glu Thr Leu Lys Asp Thr Pro Ala Pro Arg Leu Leu Lys Thr
 1               5                  10                  15

His Leu Pro Leu Ala Leu Leu Pro Gln Thr Leu Leu Asp Gln Lys Val
            20                  25                  30

Lys

<210> SEQ ID NO 33
<211> LENGTH: 42
<212> TYPE: PRT
<213> ORGANISM: Homo sapiens

<400> SEQUENCE: 33

Val Val Tyr Val Ala Arg Asn Ala Lys Asp Val Ala Val Ser Tyr Tyr
 1               5                  10                  15

His Phe Tyr His Met Ala Lys Val His Pro Glu Pro Gly Thr Trp Asp
            20                  25                  30

Ser Phe Leu Glu Lys Phe Met Val Gly Glu
        35                  40

<210> SEQ ID NO 34
<211> LENGTH: 32
<212> TYPE: PRT
<213> ORGANISM: Homo sapiens

<400> SEQUENCE: 34

Val Ser Tyr Gly Ser Trp Tyr Gln His Val Gln Glu Trp Trp Glu Leu
 1               5                  10                  15

Ser Arg Thr His Pro Val Leu Tyr Leu Phe Tyr Glu Asp Met Lys Glu
            20                  25                  30

<210> SEQ ID NO 35
<211> LENGTH: 60
<212> TYPE: PRT
<213> ORGANISM: Homo sapiens

<400> SEQUENCE: 35

Asn Pro Lys Arg Glu Ile Gln Lys Ile Leu Glu Phe Val Gly His Ser
 1               5                  10                  15

Leu Pro Glu Glu Thr Val Asp Phe Met Val Gln His Thr Ser Phe Lys

```
                    20                  25                  30
Glu Met Lys Lys Asn Pro Met Thr Asn Tyr Thr Thr Val Pro Gln Glu
                35                  40                  45

Phe Met Asp His Ser Ile Ser Pro Phe Met Arg Lys
        50                  55                  60

<210> SEQ ID NO 36
<211> LENGTH: 36
<212> TYPE: PRT
<213> ORGANISM: Homo sapiens

<400> SEQUENCE: 36

Gly Met Ala Gly Asp Trp Lys Thr Thr Phe Thr Val Ala Gln Asn Glu
 1               5                  10                  15

Arg Phe Asp Ala Asp Tyr Ala Glu Lys Met Ala Gly Cys Ser Leu Ser
                20                  25                  30

Phe Arg Ser Glu
        35

<210> SEQ ID NO 37
<211> LENGTH: 8397
<212> TYPE: DNA
<213> ORGANISM: Homo sapiens
<220> FEATURE:
<221> NAME/KEY: CDS
<222> LOCATION: (3730)...(3879)
<221> NAME/KEY: CDS
<222> LOCATION: (3987)...(4112)
<221> NAME/KEY: CDS
<222> LOCATION: (4198)...(4293)
<221> NAME/KEY: CDS
<222> LOCATION: (6088)...(6213)
<221> NAME/KEY: CDS
<222> LOCATION: (6309)...(6404)
<221> NAME/KEY: CDS
<222> LOCATION: (7214)...(7393)
<221> NAME/KEY: CDS
<222> LOCATION: (7516)...(7629)

<400> SEQUENCE: 37
ctctccctcc ttgtctctta cctgcctgct gcctgggaca ggatgaagcg gggcccttgt      60
gttgccccaa ccctggctgt tggctaagag cccacgtgat ctgcctgtga gaggagttcc    120
ttccggaaga accagggcag cttctgcccc tagagggcca atgccctagc tgagtgcagt    180
cccccggccc cagcctggtc cagctttggg aagagggtgc ccagttgtgc aatccaggcc    240
ggggcagccg tgtcctgatc ttggtattca gggctgagcc tggaggggc ttgtgatgcc     300 tgactctgtc tctctctctg gccccatgcc ttggtagctg tgaggcgtca ctgctttggg    360
tgacctgatc tggctgtgat ggatgagcac ggggggaaata gtggaagact cggaattaga   420
agacgtgagt gggctttggc cccagcctcc tacccccact ccctgtcctg ggctgcctgt    480
gaccaacctt gtttctgcag gcacactgga tagccctgct ggagctcagt gtccctaatc    540
ccctccagat actggtggcc taggggaggt catcaaagac cagtgggaca tcgacctcag    600
cctgtttcca cgtttcttgt tgttttttttt tttttgtgga gacagagttt cactcttgtt   660
gcccaggctg gagtgcaatg gcgtgatctt ggctcaccgc aacctctgcc tcccgggttc    720
aagcgattct cctgcctcag cctcccaagt agctgggatt acaggcgtgt gccaccaggc    780
ttgactaatt ttctattttt agtagagaca aggtttctcc atgttggtca ggctggtctc    840
aaactcccga cttcaggtga tctgcctgcc tcggcctccc aaagtgctgg gattacagga    900
gtgagccacc gtgccaggcc ttctccaggc tcttggcacc ttagccagaa acaatttaag    960
```

```
gacaagtgca aaagtcatga acgtaggcag atttcctgca gagtaaaggg actcactgaa   1020
gaagaggaac gtgggggtcc tcaagagagt gtctcatgcc ctacaaggtg tggggctgac   1080
ctttatgggc ttcttcaact aaagagggt atattcatga agagtccagg aaaaggtaaa   1140
gatttctcaa gaccgtggtg ccacaattta cacccaaata caggtgttcc tggagccgtc   1200
ttggcactgg tgggtgtacg gtttcatatg ttactgattg tacagtgaga tcctaggtga   1260
aacctacatc aaatacagcg ccatgttgct tctggttggt cgcagccagc ttggtcctca   1320
tcctattttt cagggactta ttggcccttg gcacatgcag ctatttcaag tttccttctt   1380
ctggtcatgt gaaactgctg cctgggattt tctgttgtct tgctagcact ctattaatct   1440
cacattctcg cctcttttct gtgccacccc ctgctggtcc ggctggtttt cactagagtg   1500
caatacaaag tctcagtcaa gagggcctcc tgaaggttgc tgagggcagg ggtggagcta   1560
gtagccggag gacctgccag tcatggggat tcctcagggg cacagaggag ggaggagggg   1620
cctgtggccc tagcagggga gcagcctctc ctctgcctgg aaatcccatg cctcagtttt   1680
ccccgcttgc ctctgagctc acgcaaccct gggaaggctt gggagactca cctttactca   1740
gatggttgtt tacctgtctc gtgcccaggt tgaccctgga ctttaaatag tgaggacaaa   1800
gaacgaggag ggtgggggga tgcactcctt ccacgggggc ctgtggcttc caagcctcaa   1860
cctcctctgg tctctgtctg tggagcctcc ttcaaaccca tggaaagaaa agtacctgcc   1920 agggctgtg gttcttctag gatcttctat cgatgttctg tgaggtcccc agggagccat   1980
gaagctgggg ctggctccca gggcaatggg actgcagtgt ccttgttctt tcttggttct   2040
atggatccat gctctgctcc accctgccc cttcactctg cccacacgca tcactccaga   2100
ctggccttgt ggtcagagcc tggagtgcat gggctgctgg aggcctgtgg gttgcactgg   2160
gccaggaccc ctggcacctt caagactggc ctggagccag caggtaggtg acctttccag   2220
ggcctgccta tcccagcttt ctcctccaat ccctcccctc tcttgcctgg gtcaattaga   2280
gaaagcttgt cttttggagt tcaggggcag gtcaggagcc cagtgacagc tcaaaaaaaa   2340
aaccccaaaa aaaaaacccc accattgggc cctttcccct ttcattcttc tgttttctac   2400
acaccaaacc cagtcgtggc tttggagatc actttaagct tgtctccagc tggcaaacta   2460
aggagggtaa tagagaagct ccccccacccc caaccctacc ccttccttcc ggaagcaaat   2520
ctaagtccag ccccggctcc agatccctcc cacactgacc taagaaaccc tcagcacaga   2580
caacacccct gcattcccca cacaacaccc acactcagcc actgcgggcg aggagggcac   2640
gaggccaggt tcccaagagc tcaggtgagt gacacaccgg aatggccagg gacgccctca   2700
ccctgctcag cttgtggctc caacattcca gaagccgagg cctctgttat ctctgccctc   2760
tccccatgga tatcccattt cagacaaccc cggccggcct gaatcccct cccttccttt   2820 ttttttttcc ggggaggcca ggtcttgctg tcaccgaggc tggagtgctg tgggatcctg   2880
gccactgcag ccttgaattc ctgggctcaa gtgattctcc tgcctcagta gctaggacta   2940
cagaccctca ccatcctgcc tggatagttt taaaaaatat ttttaaaaga ttttagaga   3000 tggggtcttc caatgctgcc cagattggtc tccaaattct ggcctcagcc tccctagggt   3060
ctgggattac aggtggggagc caccctgccc aggatcctcc ttttgctgag tcatcacagt   3120
tttgctcatt cccacatcag gctctggccc ccaataccag ctcagttgct caatgggctg   3180
tttgtcctgg aacccagatg gactgtggcc ggcaagtgg atcacaggcc tggccagcct   3240
aggagttgcc acatgtgagg ggccgagggg ctcaaggagg ggaacatcgg ggagaggagc   3300
```

```
ctactgggtg gaggctgggg gtcccagcag gaaatggtga gacaaagggc gctggctggc    3360
aggaagacag cacaggaagg tcctagaggt tcctcagtgc agctggactc tcctggagac    3420
cttcacacac cctgacatct gggccccgtt ccacgaggt gctttcactg gtctgcacca     3480
tggcccaggc cctgggattt tgaacagctc cgcaggtgaa tgaaggtga ggccaggctg     3540 gggaaccacc acattagaac ccgacctggt tttcagcccc agccccgcca ctgactggcc    3600
ttgtgagtgc gggcaagtca ctcaacctcc ctaggcctca gtgacttccc tgaaagcaag    3660
aattccactt tcttgctgtt gtgatggtgg taagggaacg ggcctggctc tggcccctga    3720 cgcaggaac atg gag ctg atc cag gac atc tct cgc ccg cca ctg gag tac    3771
          Met Glu Leu Ile Gln Asp Ile Ser Arg Pro Pro Leu Glu Tyr
          1               5                  10 gtg aag ggg gtc ccg ctc atc aag tac ttt gca gag gca ctg ggg ccc      3819
Val Lys Gly Val Pro Leu Ile Lys Tyr Phe Ala Glu Ala Leu Gly Pro
15                  20                  25                  30 ctg cag agc ttc cag gcc cgg cct gat gac ctg ctc atc agc acc tac      3867
Leu Gln Ser Phe Gln Ala Arg Pro Asp Asp Leu Leu Ile Ser Thr Tyr
                35                  40                  45 ccc aag tcc ggt aggtgaggag ggccacccac cctctcccag gtggcagtcc          3919
Pro Lys Ser Gly
            50 ccaccttggc cagcgaggtc atgctcacct cagcctgctc acctcccatc tccctccctc    3979 tccagc acc acc tgg gtg agc cag att ctg gac atg atc tac cag ggc       4028
       Thr Thr Trp Val Ser Gln Ile Leu Asp Met Ile Tyr Gln Gly
                   55                  60
ggt gac ctg gaa aag tgt cac cga gct ccc atc ttc atg cgg gtg ccc      4076
Gly Asp Leu Glu Lys Cys His Arg Ala Pro Ile Phe Met Arg Val Pro
65                  70                  75                  80 ttc ctt gag ttc aaa gtc cca ggg att ccc tca ggt gtgtgtgtcc           4122
Phe Leu Glu Phe Lys Val Pro Gly Ile Pro Ser Gly
                85                  90 tgggtgcaag gggagtggag gaagacaggg ctggggcttc agctcaccag accttccctg    4182
acccactgct caggg atg gag act ctg aaa aac aca cca gcc cca cga ctc     4233
                Met Glu Thr Leu Lys Asn Thr Pro Ala Pro Arg Leu
                                95                  100 ctg aag aca cac ctg ccc ctg gct ctg ctc ccc cag act ctg ttg gat      4281
Leu Lys Thr His Leu Pro Leu Ala Leu Leu Pro Gln Thr Leu Leu Asp
105                 110                 115                 120 cag aag gtc aag gtgagactgg gcacagtggt tcacaccgc aatctcagta           4333
Gln Lys Val Lys ctttgggagg ctgaggtggg aagatccctt gaagccagaa gttccagata agtctcttcc    4393
aaaaaaaaaa cttagctgtg catagtggtg tgtgcctgta ataccagtta ctcaggaggt    4453
tgaggtggga ggatcatctg agcctaggag tttaaggtta cagcgagcta tgatcacacc    4513
agtgcactcc aggctgggtg acagagaaac actgtctcaa aaaacgatga atagaaagag    4573
tgtcccacca gtgcggtggc tcacacctgt aattccagca cttgaagagg ctgaggcagg    4633
tggatcacct gagactagga gtttgagatc agcctggcca acatggcaaa accccatctc    4693
tactaaaaat acaaaaaaat tagccgggca tggtggcagg catctgtaat cccagctact    4753
tgggaggctg aagcaggaga attgcttgaa gctgggaggc agaggttgta gtcagccgag    4813
acctcaccat tgcaccgcag cctgggaaac aagagcaaaa ctctgtctca aaaaaaaag    4873 aaaaaaataa aaaagcggca ggtggcaggg ggctgggcct gttgtggctc acgcctgtaa    4933
taccagcact ttcggaggtc gaggtgggca gatcacccaa ggttaggagt ttgagatcag    4993
tctggccaac atggagaaac cccgtctcta ctaaaaatac aaaaattagc caggcgttgg    5053
```

-continued

```
ggcaggcgcc agtaatccca gctactcggg aggctgagga aggagaatag cttgcacctg    5113
ggaggcggtg gttgcagtga gccgagattg tgccactgta ctccagcctg ggagacacaa    5173
cgagacattg tttcaaacaa aacaaataaa tattttaaaa ggtttgccac ctgggtggct    5233
caccgctgta atgccagcat tttgggaggc caagatgggt ggaccgcttg agctcaggag    5293
ttccagacca gcccaggaaa catggggaga ctccatctct ataaagatg caaataatca    5353 gcagggcatg gtggcatagc gctatagtcc cagctactca aaagtctaag gttggaggat    5413
tgcttgagcc tgggaggtca acgttgcagt gagctattct cactccagtg cactccaacc    5473
tgggcaacag gaaaaagaa agcccaaggt cttttttctc ttttctcttt tttttgagac      5533
ctagagtccc cccccccaaa aaaaaaaaaa ccacaacaaa aagaaaaaag caaaggtcca    5593
ggtgtggggc atgtgaatcc agggaaggag gccccggctc agcccagctt tggtcctgtt    5653
cttctgggag agtcgcctca cttcctccag acttgtctca tcttccacgg ggggactgt    5713 ctgccttttg ctctgatgac caaaaacatg agactcttcc gggtagacct aagaaaggta    5773
gagggtgggt cctcacagac ccacaaaatt tggtggtggt gggaacatgc ctggtggagc    5833
atgccttgct ccagatcggg gtgtgacgca ttgatgcaga ttatattact atagaatatg    5893
atggtctcag ggaccaggca ggactttggc ttttgagcag ggttcagatc ctgacttggc    5953
cctacctgtg ccgtgagatc tcaaacaagt cagcctctaa gcctcagctt cctcctttgc    6013
caaaccaaga gatgagctgg cctggggcag gctgtgtggt gatggtgctg ggttgagtc     6073 ttctgcccct gcag gtg gtc tat gtt gcc cgc aac gca aag gat gtg gcg      6123
              Val Val Tyr Val Ala Arg Asn Ala Lys Asp Val Ala
                  125                 130                 135 gtt tcc tac tac cac ttc tac cac atg gcc aaa gtg tac cct cac cct      6171
Val Ser Tyr Tyr His Phe Tyr His Met Ala Lys Val Tyr Pro His Pro
            140                 145                 150 ggg acc tgg gaa agc ttc ctg gag aag ttc atg gct gga gaa              6213
Gly Thr Trp Glu Ser Phe Leu Glu Lys Phe Met Ala Gly Glu
        155                 160                 165 ggtgggcttg atgggaggaa ggaaggtgtg gagctaaggg gtggtggcta caacgcacag    6273
caaccctgtg tcggcacccc ctgcccgctt ctcca gtg tcc tat ggg tcc tgg       6326
                                    Val Ser Tyr Gly Ser Trp
                                                    170 tac cag cac gtg caa gag tgg tgg gag ctg agc cgc acc cac cct gtt      6374
Tyr Gln His Val Gln Glu Trp Trp Glu Leu Ser Arg Thr His Pro Val
    175                 180                 185 ctc tac ctc ttc tat gaa gac atg aag gag gtgagaccgc ctttgatgct        6424
Leu Tyr Leu Phe Tyr Glu Asp Met Lys Glu
    190                 195 tccctccacg tgacacctgg ggcaggcac ttcacaggga cctgccaagg ccacccagcc      6484
accctccctg gcggcccct ccagcaggcc cggattcccc atcctgactc cctggcccag      6544
gccccactgc agccccatgt ggcagcaggc tgggcacagc tctcatctcc tgtgcctgag    6604
tcagctgcac gggtggccat ggatcagcta cttttttttt tgagacaaaa gtcttgctct    6664
gttgtccagg atggcatgca gtggtgtgat ctcagctcag tgtaacccc cctcccaggt    6724 tcaagtgatt ctcctgcctc agcctcctga gtagctgaga ttacagatgc acactaccat    6784
gcctggctaa ttttgtgtt gtgccatgtt ggccaggttg tctccatct cctgagctca    6844 ggtgatccgc ctgcctcagc ctcccaaagt cttgggaatt acacgcctga accacggccc    6904
cttgccacag atcagctatc tattccaatt gcttctccct gccaatggtt atgccaccca    6964
```

-continued

```
gggccacagg cacggaagaa gaccatccca gtccttaccc ataggagcca agcccagctc    7024
atgatgggat cacagggcag acagcaattc attttgcccc agggactggg gtcccagggg    7084
tcgaggagct ggctctatgg gttttgaagt ggaagtggcc agttccctc tgaggttaga     7144 gaagtggacc cctttttattt tcctgaatca gcaatccaag cctccactga ggagccctct   7204
```

```
gctgctcag aac ccc aaa agg gag att caa aag atc ctg gag ttt gtg ggg   7255
         Asn Pro Lys Arg Glu Ile Gln Lys Ile Leu Glu Phe Val Gly
                 200                 205                 210 cgc tcc ctg cca gag gag act gtg gac ctc atg gtt gag cac acg tcg    7303
Arg Ser Leu Pro Glu Glu Thr Val Asp Leu Met Val Glu His Thr Ser
    215                 220                 225 ttc aag gag atg aag aag aac cct atg acc aac tac acc acc gtc cgc    7351
Phe Lys Glu Met Lys Lys Asn Pro Met Thr Asn Tyr Thr Thr Val Arg
    230                 235                 240 cgg gag ttc atg gac cac agc atc tcc ccc ttc atg agg aaa            7393
Arg Glu Phe Met Asp His Ser Ile Ser Pro Phe Met Arg Lys
245                 250                 255
```

```
ggtaggtgcc ggccagcacg ggggtttgga gcaggtggga gcagcagctg gagcctcccc   7453
ataggcactc ggggcctccc ctgggatgag actccagctt tgctccctgc cttcctcccc   7513
```

```
ca ggc atg gct ggg gac tgg aag acc acc ttc acc gtg gcg cag aat     7560
   Gly Met Ala Gly Asp Trp Lys Thr Thr Phe Thr Val Ala Gln Asn
       260                 265                 270 gag cgc ttc gat gcg gac tat gcg gag aag atg gca ggc tgc agc ctc    7608
Glu Arg Phe Asp Ala Asp Tyr Ala Glu Lys Met Ala Gly Cys Ser Leu
    275                 280                 285 agc ttc cgc tct gag ctg tga gaggggttcc tggagtcact gcagagggag       7659
Ser Phe Arg Ser Glu Leu
290                 295
```

```
tgtgcgaatc aagcctgacc aagaggctcc agaataaagt atgatttgtg ttcaatgcag   7719
agtctctatt ccaagccaag agaaaccctg agctgaaaga gtgatcgccc actggggcca   7779
aatacggcca cctccccgct ccagctcctc aacttgccct gtttggagag ggagagggt    7839 ctggagaagt aaaacccagg agacgagtag aggggggaatg tgtttaatcc cagcacgtcc  7899
tctgctgtcc tgccctgtgt cgttggggga tggcgagtct gccaggcggc atcattttt    7959 cttgggttcc ttacaagcca ccacgtatct ctgagccaca ttgaggggag gggaatagcc   8019
atctgcatag gaggtgtctt caaacaggac cgagtagtca tcctggggct gtggggcagg   8079
cagacaggag gggctgctca gagaccccca ggccaggaca ggcacccct tcccccagcc    8139 tagaccacag gaggctctgg gccgtggact ctcagccact cctaacatcc ttcactctgg   8199
ggtcaagaag tcttggccca gtccctgctg ctacagagct cttttctcag tggctggaga   8259
cccaaggcag ggaataggca gggaggagta ggggtgctga ctcccttcct agtggggtca   8319
tagctggagg gtctgctgcc tttcaaggac tctttgttga gaggactgag ggcaacccag   8379
agggtggcag gcagggat                                                 8397
```

```
<210> SEQ ID NO 38
<211> LENGTH: 50
<212> TYPE: PRT
<213> ORGANISM: Homo sapiens

<400> SEQUENCE: 38

Met Glu Leu Ile Gln Asp Ile Ser Arg Pro Pro Leu Glu Tyr Val Lys
1               5                   10                  15

Gly Val Pro Leu Ile Lys Tyr Phe Ala Glu Ala Leu Gly Pro Leu Gln
            20                  25                  30
```

```
Ser Phe Gln Ala Arg Pro Asp Asp Leu Leu Ile Ser Thr Tyr Pro Lys
        35                  40                  45

Ser Gly
    50

<210> SEQ ID NO 39
<211> LENGTH: 42
<212> TYPE: PRT
<213> ORGANISM: Homo sapiens

<400> SEQUENCE: 39

Thr Thr Trp Val Ser Gln Ile Leu Asp Met Ile Tyr Gln Gly Gly Asp
1               5                   10                  15

Leu Glu Lys Cys His Arg Ala Pro Ile Phe Met Arg Val Pro Phe Leu
            20                  25                  30

Glu Phe Lys Val Pro Gly Ile Pro Ser Gly
        35                  40

<210> SEQ ID NO 40
<211> LENGTH: 32
<212> TYPE: PRT
<213> ORGANISM: Homo sapiens

<400> SEQUENCE: 40

Met Glu Thr Leu Lys Asn Thr Pro Ala Pro Arg Leu Leu Lys Thr His
1               5                   10                  15

Leu Pro Leu Ala Leu Leu Pro Gln Thr Leu Leu Asp Gln Lys Val Lys
            20                  25                  30

<210> SEQ ID NO 41
<211> LENGTH: 42
<212> TYPE: PRT
<213> ORGANISM: Homo sapiens

<400> SEQUENCE: 41

Val Val Tyr Val Ala Arg Asn Ala Lys Asp Val Ala Val Ser Tyr Tyr
1               5                   10                  15

His Phe Tyr His Met Ala Lys Val Tyr Pro His Pro Gly Thr Trp Glu
            20                  25                  30

Ser Phe Leu Glu Lys Phe Met Ala Gly Glu
        35                  40

<210> SEQ ID NO 42
<211> LENGTH: 32
<212> TYPE: PRT
<213> ORGANISM: Homo sapiens

<400> SEQUENCE: 42

Val Ser Tyr Gly Ser Trp Tyr Gln His Val Gln Glu Trp Trp Glu Leu
1               5                   10                  15

Ser Arg Thr His Pro Val Leu Tyr Leu Phe Tyr Glu Asp Met Lys Glu
            20                  25                  30

<210> SEQ ID NO 43
<211> LENGTH: 60
<212> TYPE: PRT
<213> ORGANISM: Homo sapiens

<400> SEQUENCE: 43

Asn Pro Lys Arg Glu Ile Gln Lys Ile Leu Glu Phe Val Gly Arg Ser
1               5                   10                  15
```

Leu Pro Glu Glu Thr Val Asp Leu Met Val Glu His Thr Ser Phe Lys
            20                  25                  30

Glu Met Lys Lys Asn Pro Met Thr Asn Tyr Thr Thr Val Arg Arg Glu
            35                  40                  45

Phe Met Asp His Ser Ile Ser Pro Phe Met Arg Lys
            50                  55                  60

<210> SEQ ID NO 44
<211> LENGTH: 37
<212> TYPE: PRT
<213> ORGANISM: Homo sapiens

<400> SEQUENCE: 44

Gly Met Ala Gly Asp Trp Lys Thr Thr Phe Thr Val Ala Gln Asn Glu
  1               5                  10                  15

Arg Phe Asp Ala Asp Tyr Ala Glu Lys Met Ala Gly Cys Ser Leu Ser
            20                  25                  30

Phe Arg Ser Glu Leu
            35

<210> SEQ ID NO 45
<211> LENGTH: 8447
<212> TYPE: DNA
<213> ORGANISM: Homo sapiens
<220> FEATURE:
<221> NAME/KEY: CDS
<222> LOCATION: (4361)...(4507)
<221> NAME/KEY: CDS
<222> LOCATION: (4612)...(4737)
<221> NAME/KEY: CDS
<222> LOCATION: (4827)...(4925)
<221> NAME/KEY: CDS
<222> LOCATION: (6322)...(6447)
<221> NAME/KEY: CDS
<222> LOCATION: (6543)...(6638)
<221> NAME/KEY: CDS
<222> LOCATION: (7137)...(7316)
<221> NAME/KEY: CDS
<222> LOCATION: (7439)...(7553)

<400> SEQUENCE: 45

| | | | | | |
|---|---|---|---|---|---|
| acctctgcct | cctggttcca | agcaatcctc | cttcctcacc | ctccagagta | gctgggatta | 60 |
| cacgcgcctg | ccaccgcgcc | tggcctaatt | tttgtatttt | tagtagagat | ggggggtttcc | 120 |
| aaccatgttg | gccaggctgg | tctccaaact | cctgacctca | ggtgatcctg | cccacctaag | 180 |
| cctcccaaaa | tgctggtatt | acaggcatga | gccaccgtgc | ccggcctaaa | taattaataa | 240 |
| aataatggac | gatgggtgcc | ttctactgag | ctcccgtaa | ttgtgagtga | gtagaggact | 300 |
| tgccctgggg | acattcagtg | acctgctggg | tgttgctgag | ctgtgaggaa | gttcaggtct | 360 |
| ggctgcagtg | tgaggctgt | gactcaatca | atcactgctg | atgctcccag | gacctgcacc | 420 |
| agcttagtcc | tagggcaag | gatttaact | gtccacctca | gtttcttcat | ttgtaagatg | 480 |
| caaataacag | tcaccctgc | ctcatgggat | ggagctgtgt | aatgcccgca | acagtgcctg | 540 |
| ctgcatagag | gggttgctgc | cagctgcctc | tccctccttg | tctcttacct | gcctgctgcc | 600 |
| tgggtcagga | tgaagagggg | cccttgtgtt | gcccccaccc | tggctgcctg | ctaagggccc | 660 |
| atgtgatctg | cctggcagag | gagtttcttc | aggaagaacc | agggcagctt | ctgcccctag | 720 |
| agggccaatg | cccttggtga | gtgcagtccc | ctggccccag | cctggtccac | ctctgggaag | 780 |
| agggtgccca | gttgtgcaat | ccaggcccag | gcagctgagc | cctcatctca | gcatgcaggg | 840 |
| cggatactgg | aggggcttg | tggcatctga | ctctgtatct | cctacctgcc | cctctccttg | 900 |

-continued

```
gtagctgtga gaagtcactg ctttggggag acctgatctg gctgtgccag atggacactg      960
agaaagaagt agaagactca gaattagaag aggtgagtgg gctttggtgg cgggctccct     1020
acccccactcc ctgccctggg ctgcctgtga ccacactgct tgcctctgca ggcacactgg     1080
acagacctgc tggagacctg atcctcagtg tccttacccc ctcctacctc ttttctgtgc     1140
cacctgctgt gggtccagca ggtttttact tgagtacaat aaaaagtctg agtcaagggt     1200
gccttatggt ggatgctgag gggaggggcg gagctagtag cccaaggtcc tgccagtcac     1260
ggggcttcct caggggcaca gaggaggcag gaggggcccc tggccctagc acgtgaacag     1320
cttctactct gcctggaaac cccatgcctc agctttcccc tacttgcctc tgagctcatg     1380
caattcttgg aagcctggga gacttacctt gaaattgaat gcaaatagga caagaccaa      1440
ggaggatggg gggatgccct ccttccacgg ggccctgtgg cttccaagtc ttaatctcct     1500
ctagtctctt gtctacggag cctccttcaa acccagggaa agaaaagcac ctgccagggt     1560
tgttttttctt ctaggatctt ctattgatgc tctgtgaggt cccccaggag ccatgaagct     1620
agggctggct cctagggcaa tgggactaca gtgtccttgt cctttcttat tctttctgtt     1680
cttttctttct ttcttttttt tttttttttt ttttttgag acagagtctc actctgttgc     1740
ccaggctgga gtgcagtggt gtgatcttgg ctcactgaaa cctccgcctc tgggttcaa      1800
gtgattctct tgcctcagcc tcctgagtag ctaggattac aggtgcccgc catcatgccc     1860
agctaatttt tgtattttta gtagagacag ggtttcacca tgttggccag cttggtctcg     1920
aactcctgac ctcaggtgat cctgctgcat cgacctccca aagtactggg attacaggcg     1980
tgagccacca cgctcagcct cttttcttgtt ctatatgtcc atgctctgct ccacttctgc     2040
cccttcactc tgccccacac atcactccag actggccttg tggtcagagc ctggaatgcc     2100
tgggctgctg ggggcctgtg gactgcactg ggccagaacc cctgccgcct tcaagactgg     2160
cctgtagcca gcaggtaggt gacttttccc aggccggcct atcccacctt tccctccac      2220
tcactcacct cccttgcctg ggtcaattag agaaagcttg tcggccaggc atggtggctc     2280
atgcctgtaa tctcagcact ttgggaggcc gaggcgggcg gatcatctga gctcaggagt     2340
ttgagaccag cctggccaac atggcaaaac cccgtctcta ctaaaaatac aaaaattaac     2400
cggatgtggt ggtgtgcacc tgtaatccca gctactcgga aggctgaggc agaagaatcg     2460
cttgaaccca ggaggggggag gttacagtga gcggagatcg tgctactgca ttgcagcctg     2520
ggcgagagag cgagtctcca tctcacataa aaaaagaaa aagaaagaaa gcaagcttgt      2580
ctgttggcct gccctgcagg gtggagttca gagggaaggt caggagccta gtgacagctc     2640
aaaaaaaaaa aaacccaaat accaatgttg gccccttttg cctttcattc atgtgttttc     2700
tatacactaa actcacatat tgggtttgca gatcactcca agcttggctg gagctgtggt     2760
ggtaaggagg gtaatagaga agcttcccca ccctcaaccc cacccccttcc ttcctggagt     2820
tcccagccct gactttagat ccctcccaca ctggaccttc aaaaccctca gggcagagag     2880
cagccctaca ctccctacac cacacccata ctcagccccct gcaggcaagg agagaacagg     2940
tcaggttccc gagagctcag gtgagtgaca cgttggaatg gcccagggca ccttcaccct     3000
gctcagcttg tggctccaac attctagaag ccgaggcctc tgccatccct gccctttccc     3060
atggatattc catttcaatt agacaaccca gcctggccgg aatcccctg cgttccttct       3120
tttccttttgt gtattttga dacagggtgt gctccgtca cccaggctgg agtgtagtgg       3180
gatcctggcc cactgcagcc tcaaattcct aggctgaggc aatcctgccg cctcagcctc     3240
```

```
ctgagtagct ggggttacaa gagcaagcca ccacacccag ctaattttga aaaatatttt    3300
ttgtagagga gaggtcttgc tttgttgtcc aggttggtct caaactccag ggctcaaggg    3360
atcctttccc gttggcctcc caaggctctg ggattacagg cgggagtcac cctgcctggg    3420
cccctccttt tgatgagtca tcagttttca ttcccgcacg aggctctagc ccctggtacc    3480
agcttagttg ctcaatgggc tgtgtttgtt ctggagccca gatggactgt ggccaggcaa    3540
gtggatcaca gacctggccg gcctgggagg tttccacatg tgagggcat gagggggct     3600 caaggagggg agcatcgggg agaggagcgc actgggtgga ggctgggggt cccagcagga    3660
aatggtgaga caaagggcgc tggctggcag ggagacagca caggcaggcc ctagagcttc    3720
ctcagcacag ctggactctc ctggagacct tcacacaccc tgatatctgg gccccgcgct    3780
acgagggtgc tttcactggt ctgcactatg ccccaggccc tgggattttg aacagctctg    3840
caggtgacta aaaggtgcgg ccaggctggg aacgacctg gtttcagccc agccccgcc    3900 actgactgac tttgtgagtg cgggcaagtc actcagcctc cctaggcctc agtgacttcc    3960
ctgaaagcaa aaactctgca aaggggcagc tgggtgctgg ctcacacctg taatcccagc    4020
actttgggag gctgaggtag acaaatcact tgaggccagg agttctagac cagcctggcc    4080
aacatggtga aaccccatct ctactaaaga aaaaaaaaa ttagctgagc atggttgtac    4140
atgcttgtaa tcccagctac ttgggatgcc gaggcgggag gattgcttga acccaagagg    4200
tggagtttgc agtgagctga gattgtgcca cactgcactc cagcttgggt gagagtgaga    4260
ctccatctca aaaaaaaaa aaaaaagaga gaatcccact ttcttgctgt tgtgatggtg    4320
gtaagggaac gggcctggct ctggcccctg atgcaggaac atg gag ctg atc cag    4375
                                             Met Glu Leu Ile Gln
                                              1               5 gac acc tcc cgc ccg cca ctg gag tac gtg aag ggg gtc ccg ctc atc    4423
Asp Thr Ser Arg Pro Pro Leu Glu Tyr Val Lys Gly Val Pro Leu Ile
             10                  15                  20 aag tac ttt gca gag gca ctg ggg ccc ctg cag agc ttc caa gcc cga    4471
Lys Tyr Phe Ala Glu Ala Leu Gly Pro Leu Gln Ser Phe Gln Ala Arg
         25                  30                  35 cct gat gac ctg ctc atc aac acc tac ccc aag tct ggtaagtgag         4517
Pro Asp Asp Leu Leu Ile Asn Thr Tyr Pro Lys Ser
         40                  45 gagggccacc caccctctcc caggcggcag tccccacctt ggtcagcaag gtcgtgccct    4577
cagcctgctc acctcctatc tccctccctc tcca ggc acc acc tgg gtg agc cag    4632
                                     Gly Thr Thr Trp Val Ser Gln
                                              50                 55 ata ctg gac atg atc tac cag ggc ggc gac cta gag aag tgt aac cgg    4680
Ile Leu Asp Met Ile Tyr Gln Gly Gly Asp Leu Glu Lys Cys Asn Arg
         60                  65                  70 gct ccc atc tac gta cgg gtg ccc ttc ctt gag gtc aat gat cca ggg    4728
Ala Pro Ile Tyr Val Arg Val Pro Phe Leu Glu Val Asn Asp Pro Gly
         75                  80                  85 gaa ccc tca ggtgcatggc tgggtcctgg gggtaaggga agtggaggaa              4777
Glu Pro Ser
         90 gacagggctg ggcttcagc tcaccagacc ttccctgacc cactactca ggg ctg gag    4835
                                                       Gly Leu Glu act ctg aaa gac aca ccg ccc cca cgg ctc atc aag tca cac ctg ccc    4883
Thr Leu Lys Asp Thr Pro Pro Pro Arg Leu Ile Lys Ser His Leu Pro
 95                 100                 105                 110 ctg gct ctg ctc cct cag act ctg ttg gat cag aag gtc aag             4925
Leu Ala Leu Leu Pro Gln Thr Leu Leu Asp Gln Lys Val Lys
```

-continued

```
                  115                 120
gtgaggccgg cctcaatggt tcacacctgt catcccagtt tgagactgag gagggaggat       4985
cccttgaagg cgagagatgg agaccagcct gggcaacatt gctgtagaga tgacatccca       5045
tctctacaaa aataaaatta acaacctggt atggtggcat agactgttcc cagttactta       5105
ggaggctcag cggggaggac tgtttatgca ataggaagc tgcaatgagc cctgatgatc        5165
ctgctgctgc actccagcct gggcaacaca gcaaaaccat ctctacgaaa aaaaagttc        5225 ccactgactg gcaaggaaag ccaggaaggg gggctcaggt gccctctcag ccatgtacct       5285
gttcttctgg aagggcctcc tcgcttctgc caggctcatc acatctttt tttttttgag        5345 acagagtctt gctctgtcac cctggctgga gtgcagtggc atgatctcag ctcactgcaa       5405
cctccgcctc cccagttcaa gtgattctcc tgcctcagcc tcctgagtag ctgggattac       5465
aggcgtgtgc taccacaccc ggctaatttt tgtattcttt ttagtagaga cggggtttca       5525
ccatgttggt caagtggatc tcaaactctt gaccttgtga tcctcctgcc tcgacctcac       5585
aaagtgctgg aattacaggc gtgagccacc gcgcctggcc ttttttttt ttgagacagt        5645 ttcactcttg ttgccgaggc tagagcgcaa tcgtgtgatc tcggttcact gcaaccaccg       5705
cctcctgggt tcaagcaatt ctcctgcttc agcctcccaa ggagctggga ttacaggtac       5765
ctgccaccac gcccggctaa ttttgtattt ttagtagaga tggggtttca ccatgttggt       5825
caggctggtc ttgaactcct gacctcaggt gatctggcac cttggcctcc caaagtgccg       5885
ggattagagg catgagccac cacgcccagc cttcatcaca tcttgagaga ggacactgtc       5945
tgcctcttgc tctgatgagg gtctgatgca aaggatagtg agtctctaca gtgcacactt       6005
aagaaaggca gcatgtgggt gctcacaggt caggcggagg aggggagct ggtggggacc        6065 aggcatgcct tgctccagat caggatatga tggcattggt gcagattata ttagtataga       6125
atatggtctc aggaaccagg caggactttg gcttccgagc agggttcaga tcccagcttg       6185
gccctacctg tgcagtgaga tctcaagcaa gtcagcctct aagcctcagg ttcctccttt       6245
gccagttcaa cagatgagct ggcctgggt gggctgtgtg gtgatggtgc tggggctggg        6305
tcctctgccc ctgcag gtg gtc tat gtt gcc cga aac cca aag gac gtg gcg       6357
               Val Val Tyr Val Ala Arg Asn Pro Lys Asp Val Ala
               125                 130                 135 gtc tcc tac tac cat ttc cac cgt atg gaa aag gcg cac cct gag cct        6405
Val Ser Tyr Tyr His Phe His Arg Met Glu Lys Ala His Pro Glu Pro
        140                 145                 150 ggg acc tgg gac agc ttc ctg gaa aag ttc atg gct gga gaa                6447
Gly Thr Trp Asp Ser Phe Leu Glu Lys Phe Met Ala Gly Glu
        155                 160                 165 ggtgggcttg actggaggaa ggagggtgtg aagccgaggg gtggtggcta taacgtacag       6507
caaccctgtg tcggtgcccc ctgcccgctt ctcta gtg tcc tac ggg tcc tgg         6560
                                      Val Ser Tyr Gly Ser Trp
                                                        170 tac cag cac gtg cag gag tgg tgg gag ctg agc cgc acc cac cct gtt       6608
Tyr Gln His Val Gln Glu Trp Trp Glu Leu Ser Arg Thr His Pro Val
        175                 180                 185 ctc tac ctc ttc tat gaa gac atg aag gag gtgagaccga ctgtgatgct         6658
Leu Tyr Leu Phe Tyr Glu Asp Met Lys Glu
    190                 195 tcccccccatg tgacacctgg ggcaggcac ctcacaggga cccaccaagg ccacccagcc       6718
ccgtccctgg gcggctccca cagcaagccc ggattcccca tcctacctcc ctggcccagg       6778
cccccccact gcagccccac ctggcagcag gctcggcaca gctttcatct tctgcacctg       6838
```

-continued

```
agtcagctgc atgggtggcc acggatcaga tacttagtcc tattgcttat cctcaccaaa    6898
gggtgtgcca cccagggcca cagtcatgga agaagaccat cccggtcctc acccataggc    6958
gccaagccct gttcatgatg ggatcacagg gcagagatca attcatttta ctccagagac    7018
tagggcccca ggggttgagg ctctttgggg tttctagggg aagtggccag atcccctctg    7078
aggttagaga gggggacccg ttttgttttg ctccactgag gagccctctg ctgctcag     7136 aac ccc aaa agg gag att caa aag atc ctg gag ttt gtg ggg cgc tcc    7184
Asn Pro Lys Arg Glu Ile Gln Lys Ile Leu Glu Phe Val Gly Arg Ser
    200                 205                 210 ctg cca gag gag acc atg gac ttc atg gtt cag cac acg tcg ttc aag    7232
Leu Pro Glu Glu Thr Met Asp Phe Met Val Gln His Thr Ser Phe Lys
215                 220                 225                 230 gag atg aag aag aac cct atg acc aac tac acc acc gtc ccc cag gag    7280
Glu Met Lys Lys Asn Pro Met Thr Asn Tyr Thr Thr Val Pro Gln Glu
                235                 240                 245 ctc atg gac cac agc atc tcc ccc ttc atg agg aaa ggtgggtgct         7326
Leu Met Asp His Ser Ile Ser Pro Phe Met Arg Lys
            250                 255 ggccagcacg ggggtttggg gcgggtggga gcagcagctg cagcctcccc ataggcactt    7386
ggggcctccc ctgggatgag actccagctt tgctccctgc cttcctcccc ca ggc atg   7444
                                                          Gly Met
                                                              260 gct ggg gac tgg aag acc acc ttc acc gtg gcg cag aat gag cgc ttc    7492
Ala Gly Asp Trp Lys Thr Thr Phe Thr Val Ala Gln Asn Glu Arg Phe
            265                 270                 275 gat gcg gac tat gcg gag aag atg gca ggc tgc agc ctc agc ttc cgc    7540
Asp Ala Asp Tyr Ala Glu Lys Met Ala Gly Cys Ser Leu Ser Phe Arg
            280                 285                 290 tct gag ctg tga g aggggctcct ggagtcactg cagagggagt gtgcgaatct      7593
Ser Glu Leu
        295 accctgacca atgggctcaa gaataaagta tgattttga gtcaggcaca gtggctcatg    7653 tctgcaatcc cagcgatttg ggaggttgag ctggtaggat cacaataggc cacgaatttg    7713 agaccagcct ggtaaaatag tgagacctca tctctacaaa gatgtaaaaa aattagccac    7773 atgtgctggc acttacctgt agtcccagct acttgggaag cagaggctgg aggatcattt    7833 cagcccagga ggttgtggat acagtgagtt atgacatgcc cattcactac agcctggatg    7893 acaagcaaga ccctccctcc aaagaaaata aagctcaatt aaaataaaat atgatttgtg    7953 ttcatgtaga gcctgtattg gaaaggaaga gaaactctga gctgaaagag tgaatgcccg    8013 gtggggccac atatggtcac ctctccccca gccttcagct ccccaggtca ccatatctgg    8073 ggagggagaa agggtttgga gaagtaaaac ccaggagatg tgtggagggg ggatgtctgt    8133 ttaatcccag cacatcctct gctgtcctgc cccaagatgg tggaggacgt cgagtccgcc    8193 gggcagcgtc actttttctt gggctcctta gaagctacca ggtacctctg gccacactg    8253 agatgagggg agtagccgcc tgcataggag gtgtcttcaa acaggatagt atagtccctc    8313 ctgggggttg tgggggtagg tggccaagga agggtagagg agcaagcccc cggggctggt    8373 tgtcaactca ctttgttggc tggaattggt tgtaacttga ccacctcggg caggatccca    8433 ctgctcatcc ccaa                                                     8447
```

<210> SEQ ID NO 46
<211> LENGTH: 49
<212> TYPE: PRT
<213> ORGANISM: Homo sapiens

<400> SEQUENCE: 46

Met Glu Leu Ile Gln Asp Thr Ser Arg Pro Pro Leu Glu Tyr Val Lys
 1               5                  10                  15

Gly Val Pro Leu Ile Lys Tyr Phe Ala Glu Ala Leu Gly Pro Leu Gln
                20                  25                  30

Ser Phe Gln Ala Arg Pro Asp Asp Leu Leu Ile Asn Thr Tyr Pro Lys
            35                  40                  45

Ser

<210> SEQ ID NO 47
<211> LENGTH: 42
<212> TYPE: PRT
<213> ORGANISM: Homo sapiens

<400> SEQUENCE: 47

Gly Thr Thr Trp Val Ser Gln Ile Leu Asp Met Ile Tyr Gln Gly Gly
 1               5                  10                  15

Asp Leu Glu Lys Cys Asn Arg Ala Pro Ile Tyr Val Arg Val Pro Phe
                20                  25                  30

Leu Glu Val Asn Asp Pro Gly Glu Pro Ser
            35                  40

<210> SEQ ID NO 48
<211> LENGTH: 33
<212> TYPE: PRT
<213> ORGANISM: Homo sapiens

<400> SEQUENCE: 48

Gly Leu Glu Thr Leu Lys Asp Thr Pro Pro Arg Leu Ile Lys Ser
 1               5                  10                  15

His Leu Pro Leu Ala Leu Leu Pro Gln Thr Leu Leu Asp Gln Lys Val
                20                  25                  30

Lys

<210> SEQ ID NO 49
<211> LENGTH: 42
<212> TYPE: PRT
<213> ORGANISM: Homo sapiens

<400> SEQUENCE: 49

Val Val Tyr Val Ala Arg Asn Pro Lys Asp Val Ala Val Ser Tyr Tyr
 1               5                  10                  15

His Phe His Arg Met Glu Lys Ala His Pro Glu Pro Gly Thr Trp Asp
                20                  25                  30

Ser Phe Leu Glu Lys Phe Met Ala Gly Glu
            35                  40

<210> SEQ ID NO 50
<211> LENGTH: 32
<212> TYPE: PRT
<213> ORGANISM: Homo sapiens

<400> SEQUENCE: 50

Val Ser Tyr Gly Ser Trp Tyr Gln His Val Gln Glu Trp Trp Glu Leu
 1               5                  10                  15

Ser Arg Thr His Pro Val Leu Tyr Leu Phe Tyr Glu Asp Met Lys Glu
                20                  25                  30

```
<210> SEQ ID NO 51
<211> LENGTH: 60
<212> TYPE: PRT
<213> ORGANISM: Homo sapiens

<400> SEQUENCE: 51

Asn Pro Lys Arg Glu Ile Gln Lys Ile Leu Glu Phe Val Gly Arg Ser
 1               5                  10                  15

Leu Pro Glu Glu Thr Met Asp Phe Met Val Gln His Thr Ser Phe Lys
            20                  25                  30

Glu Met Lys Lys Asn Pro Met Thr Asn Tyr Thr Thr Val Pro Gln Glu
        35                  40                  45

Leu Met Asp His Ser Ile Ser Pro Phe Met Arg Lys
    50                  55                  60

<210> SEQ ID NO 52
<211> LENGTH: 37
<212> TYPE: PRT
<213> ORGANISM: Homo sapiens

<400> SEQUENCE: 52

Gly Met Ala Gly Asp Trp Lys Thr Thr Phe Thr Val Ala Gln Asn Glu
 1               5                  10                  15

Arg Phe Asp Ala Asp Tyr Ala Glu Lys Met Ala Gly Cys Ser Leu Ser
            20                  25                  30

Phe Arg Ser Glu Leu
        35
```